(12) United States Patent
Vuagniaux et al.

(10) Patent No.: US 8,911,934 B2
(45) Date of Patent: Dec. 16, 2014

(54) NEAR FULL-GENOME ASSAY OF HCV DRUG RESISTANCE

(75) Inventors: Grégoire Vuagniaux, Lausanne (CH); Jean-Maurice Dumont, Pully (CH); Joke Snoeck, Renens (CH); Sonia Van Dooren, Meise (BE); Anne-Mieke Vandamme, Rotselaar (BE)

(73) Assignees: Debiopharm SA, Lausanne (CH); Katholieke Universiteit Leuven, Leuven (BE)

( * ) Notice: Subject to any disclaimer, the term of this patent is extended or adjusted under 35 U.S.C. 154(b) by 399 days.

(21) Appl. No.: 12/739,648

(22) PCT Filed: Oct. 31, 2008

(86) PCT No.: PCT/IB2008/002924
§ 371 (c)(1),
(2), (4) Date: Aug. 11, 2010

(87) PCT Pub. No.: WO2009/056966
PCT Pub. Date: May 7, 2009

(65) Prior Publication Data
US 2010/0311038 A1   Dec. 9, 2010

(30) Foreign Application Priority Data

Oct. 31, 2007   (WO) .................. PCT/IB2007/003304

(51) Int. Cl.
*C12Q 1/70*   (2006.01)
*C07H 21/00*   (2006.01)

(52) U.S. Cl.
CPC ...................................... *C12Q 1/707* (2013.01)
USPC .................................. 435/5; 536/24; 536/33

(58) Field of Classification Search
None
See application file for complete search history.

(56) References Cited

FOREIGN PATENT DOCUMENTS

WO   WO 02/083948 A1   10/2002

OTHER PUBLICATIONS

Yagi et al. (Journal of Medical Virology, 2005, vol. 77, p. 399-413).*
Lu et al. (Journal of Virological Methods, Mar. 2005, vol. 126, p. 139-148 in IDS on Jan. 7, 2014).*
Database EMBL "*Homo sapiens* mRNA; EST DKFZp566I1846_r1 (from clone DKFZp56611846)", EM_EST: AL038650, XP-002521967, Mar. 12, 1999.
Database EMBL, "Novel assay for predicting the risk of developing hepatocellular carcinoma (HCC) based on the detection of a type of hepatitis C virus (HCV) related to HCC, including novel primer and novel kit for the as." EM_PAT: BD340635, XP-002521968, Nov. 8, 2005.
Database EMBL, "Sequence 5 from patent EP 0318216", EM_PATI06385, XP-002521969, Feb. 16, 1995.
Database Geneseq, "Primer for hepatitis C virus antigen DNA", Geneseqn:AAV05617, XP-002521970, May 22, 1998.
Database Geneseq, "Hepatitis C virus shot interfering RNA antisense oligo, Seq ID 64", Geneseqn:AD Q31442, XP-002521966, Oct. 7, 2002.
Murayama, Mutsumi et al., "A mutation in the interferon sensitivity-determining region is associated with responsiveness to interferon-ribavirin combination therapy in chronic hepatitis patients infected with a Japan-specific subtype of hepatitis C virus genotype 1b", Journal of Medical Virology, vol. 79, No. 1, pp. 35-40, (Jan. 2007).
Yagi, Shintaro et al., "Identification of novel HCV subgenome replicating persistently in chronic active hepatitis C patients", Journal of Medical Virology, vol. 77, No. 3, pp. 399-413, (Nov. 2005).
Yildiz, Esra et al., "Molecular characterization of a full genome Turkish hepatitis C virus 1b isolate (HCV-TR1); A predominent viral form in Turkey", Virus Genes, vol. 25, No. 2, pp. 169-177, (Oct. 2002).
International Search Report for PCT/IB2008/002924, mailed Sep. 23, 2009.
International Written Opinion for PCT/IB20081002924, mailed Sep. 23, 2009.
"Journal of Virological Methods., 2005, 126, pp. 139-148".

* cited by examiner

*Primary Examiner* — Agnieszka Boesen
(74) *Attorney, Agent, or Firm* — Hoffmann & Baron, LLP

(57) ABSTRACT

The invention relates to assays for characterization of genotypic mutations of Hepatitis C Virus (HCV) showing a resistance to anti-HCV drugs.

8 Claims, 4 Drawing Sheets

SEQUENCE LISTING

<160> NUMBER OF SEQ ID NOS: 58

<210> SEQ ID NO 1
<211> LENGTH: 30
<212> TYPE: DNA
<213> ORGANISM: Artificial Sequence
<220> FEATURE:
<223> OTHER INFORMATION: Primer HCVORpolyA

<400> SEQUENCE: 1
aaaaaaaaaa aaaaaaaaaa aaaaaaaaaa        30

<210> SEQ ID NO 2
<211> LENGTH: 32
<212> TYPE: DNA
<213> ORGANISM: Artificial Sequence
<220> FEATURE:
<223> OTHER INFORMATION: Primer HCV1bOR6312

<400> SEQUENCE: 2
ggcaggagct tggactggag ccaggtcttg aa        32

<210> SEQ ID NO 3

```
<211> LENGTH: 27
<212> TYPE: DNA
<213> ORGANISM: Artificial Sequence
<220> FEATURE:
<223> OTHER INFORMATION: Primer HCV1bOR3306

<400> SEQUENCE: 3
gatgatgtcc ccacacgccg cggtgtc                                              27

<210> SEQ ID NO 4
<211> LENGTH: 30
<212> TYPE: DNA
<213> ORGANISM: Artificial Sequence
<220> FEATURE:
<223> OTHER INFORMATION: Primer HCV1bOF6974

<400> SEQUENCE: 4
ggctgtgcag tggatgaacc ggctgatagc                                           30

<210> SEQ ID NO 5
<211> LENGTH: 32
<212> TYPE: DNA
<213> ORGANISM: Artificial Sequence
<220> FEATURE:
<223> OTHER INFORMATION: Primer HCV1bOF1977

<400> SEQUENCE: 5
caaggcaact ggttcggctg tacatggatg aa                                        32

<210> SEQ ID NO 6
<211> LENGTH: 29
<212> TYPE: DNA
<213> ORGANISM: Artificial Sequence
<220> FEATURE:
<223> OTHER INFORMATION: Primer HCVOF129

<400> SEQUENCE: 6
ccgggagagc catagtggtc tgcggaacc                                            29

<210> SEQ ID NO 7
<211> LENGTH: 26
<212> TYPE: DNA
<213> ORGANISM: Artificial Sequence
<220> FEATURE:
<223> OTHER INFORMATION: Primer HCV1bIR9339

<400> SEQUENCE: 7
gggagcaggt agatgcctac ccctac                                               26

<210> SEQ ID NO 8
<211> LENGTH: 29
<212> TYPE: DNA
<213> ORGANISM: Artificial Sequence
<220> FEATURE:
<223> OTHER INFORMATION: Primer HCV1bIR6282

<400> SEQUENCE: 8
tcagtcaaca ccgtgcatat ccagtccca                                            29

<210> SEQ ID NO 9
<211> LENGTH: 29
<212> TYPE: DNA
<213> ORGANISM: Artificial Sequence
<220> FEATURE:
<223> OTHER INFORMATION: Primer HCV1bIR2770

<400> SEQUENCE: 9
```

```
tccgcacgat gcagccatct cccggtcca                                          29
```

<210> SEQ ID NO 10
<211> LENGTH: 26
<212> TYPE: DNA
<213> ORGANISM: Artificial Sequence
<220> FEATURE:
<223> OTHER INFORMATION: Primer HCV1bIF6126

<400> SEQUENCE: 10

```
gtctccccca cgcactatgt gcctga                                             26
```

<210> SEQ ID NO 11
<211> LENGTH: 29
<212> TYPE: DNA
<213> ORGANISM: Artificial Sequence
<220> FEATURE:
<223> OTHER INFORMATION: Primer HCV1bIF2523

<400> SEQUENCE: 11

```
gacgcgcgcg tctgygcctg cttrtggat                                          29
```

<210> SEQ ID NO 12
<211> LENGTH: 30
<212> TYPE: DNA
<213> ORGANISM: Artificial Sequence
<220> FEATURE:
<223> OTHER INFORMATION: Primer HCVIF278

<400> SEQUENCE: 12

```
gccttgtggt actgcctgat agggtgcttg                                         30
```

<210> SEQ ID NO 13
<211> LENGTH: 25
<212> TYPE: DNA
<213> ORGANISM: Artificial Sequence
<220> FEATURE:
<223> OTHER INFORMATION: Primer 1bSF310

<400> SEQUENCE: 13

```
gagtgccccg ggaggtcttc gtaga                                              25
```

<210> SEQ ID NO 14
<211> LENGTH: 24
<212> TYPE: DNA
<213> ORGANISM: Artificial Sequence
<220> FEATURE:
<223> OTHER INFORMATION: Primer HCV1bSF807

<400> SEQUENCE: 14

```
ccgggttctg gaggacggcg tgaa                                               24
```

<210> SEQ ID NO 15
<211> LENGTH: 26
<212> TYPE: DNA
<213> ORGANISM: Artificial Sequence
<220> FEATURE:
<223> OTHER INFORMATION: Primer HCV1bSR850

<400> SEQUENCE: 15

```
aggaagatag agaaagagca accggg                                             26
```

<210> SEQ ID NO 16
<211> LENGTH: 22
<212> TYPE: DNA

<213> ORGANISM: Artificial Sequence
<220> FEATURE:
<223> OTHER INFORMATION: Primer HCV1bSF1202

<400> SEQUENCE: 16
tctcccagct gttcaccttc tc                                          22

<210> SEQ ID NO 17
<211> LENGTH: 21
<212> TYPE: DNA
<213> ORGANISM: Artificial Sequence
<220> FEATURE:
<223> OTHER INFORMATION: Primer HCV1bSR1302

<400> SEQUENCE: 17
gaccagttca tcatcatatc c                                           21

<210> SEQ ID NO 18
<211> LENGTH: 23
<212> TYPE: DNA
<213> ORGANISM: Artificial Sequence
<220> FEATURE:
<223> OTHER INFORMATION: Primer HCV1bSF1597

<400> SEQUENCE: 18
ggcagctggc acatcaacag gac                                         23

<210> SEQ ID NO 19
<211> LENGTH: 22
<212> TYPE: DNA
<213> ORGANISM: Artificial Sequence
<220> FEATURE:
<223> OTHER INFORMATION: Primer HCV1bSR1653

<400> SEQUENCE: 19
gtagaacagc gcggcaagga ac                                          22

<210> SEQ ID NO 20
<211> LENGTH: 23
<212> TYPE: DNA
<213> ORGANISM: Artificial Sequence
<220> FEATURE:
<223> OTHER INFORMATION: Primer HV1bSF1854

<400> SEQUENCE: 20
tggtccagtg tattgyttca ccc                                         23

<210> SEQ ID NO 21
<211> LENGTH: 23
<212> TYPE: DNA
<213> ORGANISM: Artificial Sequence
<220> FEATURE:
<223> OTHER INFORMATION: Primer HCV1bSR1990

<400> SEQUENCE: 21
ttcatccatg tacagccgaa cca                                         23

<210> SEQ ID NO 22
<211> LENGTH: 22
<212> TYPE: DNA
<213> ORGANISM: Artificial Sequence
<220> FEATURE:
<223> OTHER INFORMATION: Primer HCV1bSF2242

<400> SEQUENCE: 22 gtgggggggcg tggagcacag gc                                         22

<210> SEQ ID NO 23
<211> LENGTH: 23
<212> TYPE: DNA
<213> ORGANISM: Artificial Sequence
<220> FEATURE:
<223> OTHER INFORMATION: Primer HCV1bSR2433

<400> SEQUENCE: 23
cgtacaggta ttgcacgtcc acg                                              23

<210> SEQ ID NO 24
<211> LENGTH: 23
<212> TYPE: DNA
<213> ORGANISM: Artificial Sequence
<220> FEATURE:
<223> OTHER INFORMATION: Primer HCV1bSF2640

<400> SEQUENCE: 24
tctctccttc cttgtgttct tct                                              23

<210> SEQ ID NO 25
<211> LENGTH: 23
<212> TYPE: DNA
<213> ORGANISM: Artificial Sequence
<220> FEATURE:
<223> OTHER INFORMATION: Primer HCV1bSF2860

<400> SEQUENCE: 25
aaccaccata tgagcctggc gag                                              23

<210> SEQ ID NO 26
<211> LENGTH: 22
<212> TYPE: DNA
<213> ORGANISM: Artificial Sequence
<220> FEATURE:
<223> OTHER INFORMATION: Primer HCV1bSF3085

<400> SEQUENCE: 26
cgcgctcaag ggctcatycg tg                                               22

<210> SEQ ID NO 27
<211> LENGTH: 23
<212> TYPE: DNA
<213> ORGANISM: Artificial Sequence
<220> FEATURE:
<223> OTHER INFORMATION: Primer HCV1bSR3280

<400> SEQUENCE: 27
caggtgatga tcttggtctc cat                                              23

<210> SEQ ID NO 28
<211> LENGTH: 23
<212> TYPE: DNA
<213> ORGANISM: Artificial Sequence
<220> FEATURE:
<223> OTHER INFORMATION: Primer HCV1bSF3541

<400> SEQUENCE: 28
acrcaatctt tcctggcgac ctg                                              23

<210> SEQ ID NO 29
<211> LENGTH: 24
<212> TYPE: DNA
<213> ORGANISM: Artificial Sequence
<220> FEATURE:

<223> OTHER INFORMATION: Primer HCV1bSR3643

<400> SEQUENCE: 29
gtcctggtct acattggtgt acat                                    24

<210> SEQ ID NO 30
<211> LENGTH: 22
<212> TYPE: DNA
<213> ORGANISM: Artificial Sequence
<220> FEATURE:
<223> OTHER INFORMATION: Primer HCV1bSF4004

<400> SEQUENCE: 30
cgcagacatt ccaagtggcc ca                                      22

<210> SEQ ID NO 31
<211> LENGTH: 23
<212> TYPE: DNA
<213> ORGANISM: Artificial Sequence
<220> FEATURE:
<223> OTHER INFORMATION: Primer HCV1bSR4237

<400> SEQUENCE: 31
caaccaccgt cggcaaggaa ctt                                     23

<210> SEQ ID NO 32
<211> LENGTH: 23
<212> TYPE: DNA
<213> ORGANISM: Artificial Sequence
<220> FEATURE:
<223> OTHER INFORMATION: Primer HCV1bSF4516

<400> SEQUENCE: 32
ctcattttct gccattccaa gaa                                     23

<210> SEQ ID NO 33
<211> LENGTH: 26
<212> TYPE: DNA
<213> ORGANISM: Artificial Sequence
<220> FEATURE:
<223> OTHER INFORMATION: Primer HCV1bSR4666

<400> SEQUENCE: 33
tcaaagtcgc cggtawagcc cgtcat                                  26

<210> SEQ ID NO 34
<211> LENGTH: 21
<212> TYPE: DNA
<213> ORGANISM: Artificial Sequence
<220> FEATURE:
<223> OTHER INFORMATION: Primer HCV1bSF5048

<400> SEQUENCE: 34
tagatgccca cttcttgtcc c                                       21

<210> SEQ ID NO 35
<211> LENGTH: 23
<212> TYPE: DNA
<213> ORGANISM: Artificial Sequence
<220> FEATURE:
<223> OTHER INFORMATION: Primer HCV1bSR5164

<400> SEQUENCE: 35
agccgtatga gacacttcca cat                                     23

```
<210> SEQ ID NO 36
<211> LENGTH: 23
<212> TYPE: DNA
<213> ORGANISM: Artificial Sequence
<220> FEATURE:
<223> OTHER INFORMATION: Primer HCV1bSF5524

<400> SEQUENCE: 36
caattcaagc agaaggcgct cgg                                              23

<210> SEQ ID NO 37
<211> LENGTH: 25
<212> TYPE: DNA
<213> ORGANISM: Artificial Sequence
<220> FEATURE:
<223> OTHER INFORMATION: Primer HCV1bSR5639

<400> SEQUENCE: 37
tgtatcccgc tgatgaartt ccaca                                            25

<210> SEQ ID NO 38
<211> LENGTH: 27
<212> TYPE: DNA
<213> ORGANISM: Artificial Sequence
<220> FEATURE:
<223> OTHER INFORMATION: Primer HCV1bSF5986

<400> SEQUENCE: 38
acacgctgtg ataaatgtct cccccgc                                          27

<210> SEQ ID NO 39
<211> LENGTH: 25
<212> TYPE: DNA
<213> ORGANISM: Artificial Sequence
<220> FEATURE:
<223> OTHER INFORMATION: Primer HCV1bSR6092

<400> SEQUENCE: 39
gaagcgaacg ctatcagccg gttca                                            25

<210> SEQ ID NO 40
<211> LENGTH: 24
<212> TYPE: DNA
<213> ORGANISM: Artificial Sequence
<220> FEATURE:
<223> OTHER INFORMATION: Primer HCV1bSF6186

<400> SEQUENCE: 40
cctctccagc cttaccatca ctca                                             24

<210> SEQ ID NO 41
<211> LENGTH: 26
<212> TYPE: DNA
<213> ORGANISM: Artificial Sequence
<220> FEATURE:
<223> OTHER INFORMATION: Primer HCV1bSR6256
<220> FEATURE:
<221> NAME/KEY: modified_base
<222> LOCATION: (6)..(6)
<223> OTHER INFORMATION: deoxyinosine
<220> FEATURE:
<221> NAME/KEY: misc_feature
<222> LOCATION: (6)..(6)
<223> OTHER INFORMATION: n is deoxyinosine

<400> SEQUENCE: 41
tccctnagcc acgagccgga gcatgg                                           26
```

<210> SEQ ID NO 42
<211> LENGTH: 22
<212> TYPE: DNA
<213> ORGANISM: Artificial Sequence
<220> FEATURE:
<223> OTHER INFORMATION: Primer HCV1bSF6416
<220> FEATURE:
<221> NAME/KEY: modified_base
<222> LOCATION: (8)..(8)
<223> OTHER INFORMATION: deoxyinosine
<220> FEATURE:
<221> NAME/KEY: misc_feature
<222> LOCATION: (8)..(8)
<223> OTHER INFORMATION: n is deoxyinosine

<400> SEQUENCE: 42
tcatgcanac cacctgccca tg                                    22

<210> SEQ ID NO 43
<211> LENGTH: 23
<212> TYPE: DNA
<213> ORGANISM: Artificial Sequence
<220> FEATURE:
<223> OTHER INFORMATION: Primer HCV1bSR6616

<400> SEQUENCE: 43
tcccccaccc gcgtgacctc cac                                   23

<210> SEQ ID NO 44
<211> LENGTH: 23
<212> TYPE: DNA
<213> ORGANISM: Artificial Sequence
<220> FEATURE:
<223> OTHER INFORMATION: Primer HCV1bSF6853

<400> SEQUENCE: 44
gtgctcactt ccatgctcac cga                                   23

<210> SEQ ID NO 45
<211> LENGTH: 22
<212> TYPE: DNA
<213> ORGANISM: Artificial Sequence
<220> FEATURE:
<223> OTHER INFORMATION: Primer HCV1bSR6964

<400> SEQUENCE: 45
tcaaggaagg cgcagacaac tg                                    22

<210> SEQ ID NO 46
<211> LENGTH: 23
<212> TYPE: DNA
<213> ORGANISM: Artificial Sequence
<220> FEATURE:
<223> OTHER INFORMATION: Primer HCV1bSF7066

<400> SEQUENCE: 46
gggaacatca cccgcgtgga gtc                                   23

<210> SEQ ID NO 47
<211> LENGTH: 23
<212> TYPE: DNA
<213> ORGANISM: Artificial Sequence
<220> FEATURE:
<223> OTHER INFORMATION: Primer HCV1bSR7273

<400> SEQUENCE: 47
gggcacccgt gtaccaccgg agg                                   23

<210> SEQ ID NO 48
<211> LENGTH: 23
<212> TYPE: DNA
<213> ORGANISM: Artificial Sequence
<220> FEATURE:
<223> OTHER INFORMATION: Primer HCV1bSF7504

<400> SEQUENCE: 48
tactcctcca tgcccccct tga                                              23

<210> SEQ ID NO 49
<211> LENGTH: 24
<212> TYPE: DNA
<213> ORGANISM: Artificial Sequence
<220> FEATURE:
<223> OTHER INFORMATION: Primer HCV1bSR7558

<400> SEQUENCE: 49
ctcgctcacr gtagaccaag accc                                            24

<210> SEQ ID NO 50
<211> LENGTH: 24
<212> TYPE: DNA
<213> ORGANISM: Artificial Sequence
<220> FEATURE:
<223> OTHER INFORMATION: Primer HCV1bSF7968

<400> SEQUENCE: 50
ctccgtgtgg aaggacttgc tgga                                            24

<210> SEQ ID NO 51
<211> LENGTH: 23
<212> TYPE: DNA
<213> ORGANISM: Artificial Sequence
<220> FEATURE:
<223> OTHER INFORMATION: Primer HCV1bSR8077

<400> SEQUENCE: 51
tctgggaata cgataaggcg agc                                             23

<210> SEQ ID NO 52
<211> LENGTH: 22
<212> TYPE: DNA
<213> ORGANISM: Artificial Sequence
<220> FEATURE:
<223> OTHER INFORMATION: Primer HCV1bSF8528

<400> SEQUENCE: 52
agctccagga ctgcacgatg ct                                              22

<210> SEQ ID NO 53
<211> LENGTH: 24
<212> TYPE: DNA
<213> ORGANISM: Artificial Sequence
<220> FEATURE:
<223> OTHER INFORMATION: Primer HCV1bSR8622

<400> SEQUENCE: 53
tacctagtca tagcctccgt gaag                                            24

<210> SEQ ID NO 54
<211> LENGTH: 27
<212> TYPE: DNA
<213> ORGANISM: Artificial Sequence
<220> FEATURE:

<223> OTHER INFORMATION: Primer HCV1bSF9010

<400> SEQUENCE: 54
acacgctgtg ataaatgtct cccccgc  27

<210> SEQ ID NO 55
<211> LENGTH: 22
<212> TYPE: DNA
<213> ORGANISM: Artificial Sequence
<220> FEATURE:
<223> OTHER INFORMATION: Primer HCV1bSR9094

<400> SEQUENCE: 55
gatgtctcca gactcgcaag gg  22

<210> SEQ ID NO 56
<211> LENGTH: 3010
<212> TYPE: PRT
<213> ORGANISM: Hepatitis C virus con1

<400> SEQUENCE: 56

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Gln Pro Glu Gly Arg Ala Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
            180                 185                 190

Glu Val Arg Asn Val Ser Gly Val Tyr His Val Thr Asn Asp Cys Ser
        195                 200                 205

Asn Ala Ser Ile Val Tyr Glu Ala Ala Asp Met Ile Met His Thr Pro
    210                 215                 220

Gly Cys Val Pro Cys Val Arg Glu Asn Asn Ser Ser Arg Cys Trp Val
225                 230                 235                 240

Ala Leu Thr Pro Thr Leu Ala Ala Arg Asn Ala Ser Val Pro Thr Thr
                245                 250                 255

Thr Ile Arg Arg His Val Asp Leu Leu Val Gly Ala Ala Ala Leu Cys
            260                 265                 270

Ser Ala Met Tyr Val Gly Asp Leu Cys Gly Ser Val Phe Leu Val Ala
        275                 280                 285
```

-continued

```
Gln Leu Phe Thr Phe Ser Pro Arg Arg His Glu Thr Val Gln Asp Cys
    290                 295                 300

Asn Cys Ser Ile Tyr Pro Gly His Val Thr Gly His Arg Met Ala Trp
305                 310                 315                 320

Asp Met Met Met Asn Trp Ser Pro Thr Ala Ala Leu Val Val Ser Gln
                325                 330                 335

Leu Leu Arg Ile Pro Gln Ala Val Val Asp Met Val Ala Gly Ala His
            340                 345                 350

Trp Gly Val Leu Ala Gly Leu Ala Tyr Tyr Ser Met Val Gly Asn Trp
        355                 360                 365

Ala Lys Val Leu Ile Val Met Leu Leu Phe Ala Gly Val Asp Gly Gly
    370                 375                 380

Thr Tyr Val Thr Gly Gly Thr Met Ala Lys Asn Thr Leu Gly Ile Thr
385                 390                 395                 400

Ser Leu Phe Ser Pro Gly Ser Ser Gln Lys Ile Gln Leu Val Asn Thr
                405                 410                 415

Asn Gly Ser Trp His Ile Asn Arg Thr Ala Leu Asn Cys Asn Asp Ser
            420                 425                 430

Leu Asn Thr Gly Phe Leu Ala Ala Leu Phe Tyr Val His Lys Phe Asn
        435                 440                 445

Ser Ser Gly Cys Pro Glu Arg Met Ala Ser Cys Ser Pro Ile Asp Ala
    450                 455                 460

Phe Ala Gln Gly Trp Gly Pro Ile Thr Tyr Asn Glu Ser His Ser Ser
465                 470                 475                 480

Asp Gln Arg Pro Tyr Cys Trp His Tyr Ala Pro Arg Pro Cys Gly Ile
                485                 490                 495

Val Pro Ala Ala Gln Val Cys Gly Pro Val Tyr Cys Phe Thr Pro Ser
            500                 505                 510

Pro Val Val Gly Thr Thr Asp Arg Phe Gly Val Pro Thr Tyr Ser
        515                 520                 525

Trp Gly Glu Asn Glu Thr Asp Val Leu Leu Leu Asn Asn Thr Arg Pro
    530                 535                 540

Pro Gln Gly Asn Trp Phe Gly Cys Thr Trp Met Asn Ser Thr Gly Phe
545                 550                 555                 560

Thr Lys Thr Cys Gly Gly Pro Pro Cys Asn Ile Gly Gly Ile Gly Asn
                565                 570                 575

Lys Thr Leu Thr Cys Pro Thr Asp Cys Phe Arg Lys His Pro Glu Ala
            580                 585                 590

Thr Tyr Thr Lys Cys Gly Ser Gly Pro Trp Leu Thr Pro Arg Cys Leu
        595                 600                 605

Val His Tyr Pro Tyr Arg Leu Trp His Tyr Pro Cys Thr Val Asn Phe
    610                 615                 620

Thr Ile Phe Lys Val Arg Met Tyr Val Gly Gly Val Glu His Arg Leu
625                 630                 635                 640

Glu Ala Ala Cys Asn Trp Thr Arg Gly Glu Arg Cys Asn Leu Glu Asp
                645                 650                 655

Arg Asp Arg Ser Glu Leu Ser Pro Leu Leu Leu Ser Thr Thr Glu Trp
            660                 665                 670

Gln Val Leu Pro Cys Ser Phe Thr Thr Leu Pro Ala Leu Ser Thr Gly
        675                 680                 685

Leu Ile His Leu His Gln Asn Val Val Asp Val Gln Tyr Leu Tyr Gly
    690                 695                 700
```

```
Ile Gly Ser Ala Val Val Ser Phe Ala Ile Lys Trp Glu Tyr Val Leu
705                 710                 715                 720

Leu Leu Phe Leu Leu Leu Ala Asp Ala Arg Val Cys Ala Cys Leu Trp
            725                 730                 735

Met Met Leu Leu Ile Ala Gln Ala Glu Ala Ala Leu Glu Asn Leu Val
        740                 745                 750

Val Leu Asn Ala Ala Ser Val Ala Gly Ala His Gly Ile Leu Ser Phe
            755                 760                 765

Leu Val Phe Phe Cys Ala Ala Trp Tyr Ile Lys Gly Arg Leu Val Pro
    770                 775                 780

Gly Ala Ala Tyr Ala Leu Tyr Gly Val Trp Pro Leu Leu Leu Leu Leu
785                 790                 795                 800

Leu Ala Leu Pro Pro Arg Ala Tyr Ala Met Asp Arg Glu Met Ala Ala
            805                 810                 815

Ser Cys Gly Gly Ala Val Phe Val Gly Leu Ile Leu Leu Thr Leu Ser
        820                 825                 830

Pro His Tyr Lys Leu Phe Leu Ala Arg Leu Ile Trp Trp Leu Gln Tyr
            835                 840                 845

Phe Ile Thr Arg Ala Glu Ala His Leu Gln Val Trp Ile Pro Pro Leu
850                 855                 860

Asn Val Arg Gly Gly Arg Asp Ala Val Ile Leu Leu Thr Cys Ala Ile
865                 870                 875                 880

His Pro Glu Leu Ile Phe Thr Ile Thr Lys Ile Leu Leu Ala Ile Leu
                885                 890                 895

Gly Pro Leu Met Val Leu Gln Ala Gly Ile Thr Lys Val Pro Tyr Phe
            900                 905                 910

Val Arg Ala His Gly Leu Ile Arg Ala Cys Met Leu Val Arg Lys Val
            915                 920                 925

Ala Gly Gly His Tyr Val Gln Met Ala Leu Met Lys Leu Ala Ala Leu
        930                 935                 940

Thr Gly Thr Tyr Val Tyr Asp His Leu Thr Pro Leu Arg Asp Trp Ala
945                 950                 955                 960

His Ala Gly Leu Arg Asp Leu Ala Val Ala Val Glu Pro Val Val Phe
            965                 970                 975

Ser Asp Met Glu Thr Lys Val Ile Thr Trp Gly Ala Asp Thr Ala Ala
        980                 985                 990

Cys Gly Asp Ile Ile Leu Gly Leu Pro Val Ser Ala Arg Arg Gly Arg
            995                1000                1005

Glu Ile His Leu Gly Pro Ala Asp Ser Leu Glu Gly Gln Gly Trp
    1010                1015                1020

Arg Leu Leu Ala Pro Ile Thr Ala Tyr Ser Gln Gln Thr Arg Gly
    1025                1030                1035

Leu Leu Gly Cys Ile Ile Thr Ser Leu Thr Gly Arg Asp Arg Asn
    1040                1045                1050

Gln Val Glu Gly Glu Val Gln Val Val Ser Thr Ala Thr Gln Ser
    1055                1060                1065

Phe Leu Ala Thr Cys Val Asn Gly Val Cys Trp Thr Val Tyr His
    1070                1075                1080

Gly Ala Gly Ser Lys Thr Leu Ala Gly Pro Lys Gly Pro Ile Thr
    1085                1090                1095

Gln Met Tyr Thr Asn Val Asp Gln Asp Leu Val Gly Trp Gln Ala
    1100                1105                1110

Pro Pro Gly Ala Arg Ser Leu Thr Pro Cys Thr Cys Gly Ser Ser
```

```
                1115                1120                1125

Asp Leu Tyr Leu Val Thr Arg His Ala Asp Val Ile Pro Val Arg
        1130                1135                1140

Arg Arg Gly Asp Ser Arg Gly Ser Leu Leu Ser Pro Arg Pro Val
        1145                1150                1155

Ser Tyr Leu Lys Gly Ser Ser Gly Gly Pro Leu Leu Cys Pro Ser
        1160                1165                1170

Gly His Ala Val Gly Ile Phe Arg Ala Ala Val Cys Thr Arg Gly
        1175                1180                1185

Val Ala Lys Ala Val Asp Phe Val Pro Val Glu Ser Met Glu Thr
        1190                1195                1200

Thr Met Arg Ser Pro Val Phe Thr Asp Asn Ser Ser Pro Pro Ala
        1205                1210                1215

Val Pro Gln Thr Phe Gln Val Ala His Leu His Ala Pro Thr Gly
        1220                1225                1230

Ser Gly Lys Ser Thr Lys Val Pro Ala Ala Tyr Ala Ala Gln Gly
        1235                1240                1245

Tyr Lys Val Leu Val Leu Asn Pro Ser Val Ala Ala Thr Leu Gly
        1250                1255                1260

Phe Gly Ala Tyr Met Ser Lys Ala His Gly Ile Asp Pro Asn Ile
        1265                1270                1275

Arg Thr Gly Val Arg Thr Ile Thr Thr Gly Ala Pro Ile Thr Tyr
        1280                1285                1290

Ser Thr Tyr Gly Lys Phe Leu Ala Asp Gly Gly Cys Ser Gly Gly
        1295                1300                1305

Ala Tyr Asp Ile Ile Ile Cys Asp Glu Cys His Ser Thr Asp Ser
        1310                1315                1320

Thr Thr Ile Leu Gly Ile Gly Thr Val Leu Asp Gln Ala Glu Thr
        1325                1330                1335

Ala Gly Ala Arg Leu Val Val Leu Ala Thr Ala Thr Pro Pro Gly
        1340                1345                1350

Ser Val Thr Val Pro His Pro Asn Ile Glu Glu Val Ala Leu Ser
        1355                1360                1365

Ser Thr Gly Glu Ile Pro Phe Tyr Gly Lys Ala Ile Pro Ile Glu
        1370                1375                1380

Thr Ile Lys Gly Gly Arg His Leu Ile Phe Cys His Ser Lys Lys
        1385                1390                1395

Lys Cys Asp Glu Leu Ala Ala Lys Leu Ser Gly Leu Gly Leu Asn
        1400                1405                1410

Ala Val Ala Tyr Tyr Arg Gly Leu Asp Val Ser Val Ile Pro Thr
        1415                1420                1425

Ser Gly Asp Val Ile Val Val Ala Thr Asp Ala Leu Met Thr Gly
        1430                1435                1440

Phe Thr Gly Asp Phe Asp Ser Val Ile Asp Cys Asn Thr Cys Val
        1445                1450                1455

Thr Gln Thr Val Asp Phe Ser Leu Asp Pro Thr Phe Thr Ile Glu
        1460                1465                1470

Thr Thr Thr Val Pro Gln Asp Ala Val Ser Arg Ser Gln Arg Arg
        1475                1480                1485

Gly Arg Thr Gly Arg Gly Arg Met Gly Ile Tyr Arg Phe Val Thr
        1490                1495                1500

Pro Gly Glu Arg Pro Ser Gly Met Phe Asp Ser Ser Val Leu Cys
        1505                1510                1515
```

```
Glu Cys Tyr Asp Ala Gly Cys Ala Trp Tyr Glu Leu Thr Pro Ala
1520                1525                1530

Glu Thr Ser Val Arg Leu Arg Ala Tyr Leu Asn Thr Pro Gly Leu
1535                1540                1545

Pro Val Cys Gln Asp His Leu Glu Phe Trp Glu Ser Val Phe Thr
1550                1555                1560

Gly Leu Thr His Ile Asp Ala His Phe Leu Ser Gln Thr Lys Gln
1565                1570                1575

Ala Gly Asp Asn Phe Pro Tyr Leu Val Ala Tyr Gln Ala Thr Val
1580                1585                1590

Cys Ala Arg Ala Gln Ala Pro Pro Pro Ser Trp Asp Gln Met Trp
1595                1600                1605

Lys Cys Leu Ile Arg Leu Lys Pro Thr Leu His Gly Pro Thr Pro
1610                1615                1620

Leu Leu Tyr Arg Leu Gly Ala Val Gln Asn Glu Val Thr Thr Thr
1625                1630                1635

His Pro Ile Thr Lys Tyr Ile Met Ala Cys Met Ser Ala Asp Leu
1640                1645                1650

Glu Val Val Thr Ser Thr Trp Val Leu Val Gly Gly Val Leu Ala
1655                1660                1665

Ala Leu Ala Ala Tyr Cys Leu Thr Thr Gly Ser Val Val Ile Val
1670                1675                1680

Gly Arg Ile Ile Leu Ser Gly Lys Pro Ala Ile Ile Pro Asp Arg
1685                1690                1695

Glu Val Leu Tyr Arg Glu Phe Asp Glu Met Glu Glu Cys Ala Ser
1700                1705                1710

His Leu Pro Tyr Ile Glu Gln Gly Met Gln Leu Ala Glu Gln Phe
1715                1720                1725

Lys Gln Lys Ala Ile Gly Leu Leu Gln Thr Ala Thr Lys Gln Ala
1730                1735                1740

Glu Ala Ala Ala Pro Val Val Glu Ser Lys Trp Arg Thr Leu Glu
1745                1750                1755

Ala Phe Trp Ala Lys His Met Trp Asn Phe Ile Ser Gly Ile Gln
1760                1765                1770

Tyr Leu Ala Gly Leu Ser Thr Leu Pro Gly Asn Pro Ala Ile Ala
1775                1780                1785

Ser Leu Met Ala Phe Thr Ala Ser Ile Thr Ser Pro Leu Thr Thr
1790                1795                1800

Gln His Thr Leu Leu Phe Asn Ile Leu Gly Gly Trp Val Ala Ala
1805                1810                1815

Gln Leu Ala Pro Pro Ser Ala Ala Ser Ala Phe Val Gly Ala Gly
1820                1825                1830

Ile Ala Gly Ala Ala Val Gly Ser Ile Gly Leu Gly Lys Val Leu
1835                1840                1845

Val Asp Ile Leu Ala Gly Tyr Gly Ala Gly Val Ala Gly Ala Leu
1850                1855                1860

Val Ala Phe Lys Val Met Ser Gly Glu Met Pro Ser Thr Glu Asp
1865                1870                1875

Leu Val Asn Leu Leu Pro Ala Ile Leu Ser Pro Gly Ala Leu Val
1880                1885                1890

Val Gly Val Val Cys Ala Ala Ile Leu Arg Arg His Val Gly Pro
1895                1900                1905
```

```
Gly Glu Gly Ala Val Gln Trp Met Asn Arg Leu Ile Ala Phe Ala
    1910                1915                1920

Ser Arg Gly Asn His Val Ser Pro Thr His Tyr Val Pro Glu Ser
    1925                1930                1935

Asp Ala Ala Ala Arg Val Thr Gln Ile Leu Ser Ser Leu Thr Ile
    1940                1945                1950

Thr Gln Leu Leu Lys Arg Leu His Gln Trp Ile Asn Glu Asp Cys
    1955                1960                1965

Ser Thr Pro Cys Ser Gly Ser Trp Leu Arg Asp Val Trp Asp Trp
    1970                1975                1980

Ile Cys Thr Val Leu Thr Asp Phe Lys Thr Trp Leu Gln Ser Lys
    1985                1990                1995

Leu Leu Pro Arg Leu Pro Gly Val Pro Phe Phe Ser Cys Gln Arg
    2000                2005                2010

Gly Tyr Lys Gly Val Trp Arg Gly Asp Gly Ile Met Gln Thr Thr
    2015                2020                2025

Cys Pro Cys Gly Ala Gln Ile Thr Gly His Val Lys Asn Gly Ser
    2030                2035                2040

Met Arg Ile Val Gly Pro Arg Thr Cys Ser Asn Thr Trp His Gly
    2045                2050                2055

Thr Phe Pro Ile Asn Ala Tyr Thr Thr Gly Pro Cys Thr Pro Ser
    2060                2065                2070

Pro Ala Pro Asn Tyr Ser Arg Ala Leu Trp Arg Val Ala Ala Glu
    2075                2080                2085

Glu Tyr Val Glu Val Thr Arg Val Gly Asp Phe His Tyr Val Thr
    2090                2095                2100

Gly Met Thr Thr Asp Asn Val Lys Cys Pro Cys Gln Val Pro Ala
    2105                2110                2115

Pro Glu Phe Phe Thr Glu Val Asp Gly Val Arg Leu His Arg Tyr
    2120                2125                2130

Ala Pro Ala Cys Lys Pro Leu Leu Arg Glu Glu Val Thr Phe Leu
    2135                2140                2145

Val Gly Leu Asn Gln Tyr Leu Val Gly Ser Gln Leu Pro Cys Glu
    2150                2155                2160

Pro Glu Pro Asp Val Ala Val Leu Thr Ser Met Leu Thr Asp Pro
    2165                2170                2175

Ser His Ile Thr Ala Glu Thr Ala Lys Arg Arg Leu Ala Arg Gly
    2180                2185                2190

Ser Pro Pro Ser Leu Ala Ser Ser Ser Ala Ser Gln Leu Ser Ala
    2195                2200                2205

Pro Ser Leu Lys Ala Thr Cys Thr Thr Arg His Asp Ser Pro Asp
    2210                2215                2220

Ala Asp Leu Ile Glu Ala Asn Leu Leu Trp Arg Gln Glu Met Gly
    2225                2230                2235

Gly Asn Ile Thr Arg Val Glu Ser Glu Asn Lys Val Val Ile Leu
    2240                2245                2250

Asp Ser Phe Glu Pro Leu Gln Ala Glu Glu Asp Glu Arg Glu Val
    2255                2260                2265

Ser Val Pro Ala Glu Ile Leu Arg Arg Ser Arg Lys Phe Pro Arg
    2270                2275                2280

Ala Met Pro Ile Trp Ala Arg Pro Asp Tyr Asn Pro Pro Leu Leu
    2285                2290                2295

Glu Ser Trp Lys Asp Pro Asp Tyr Val Pro Pro Val Val His Gly
```

```
            2300                2305                2310
Cys Pro Leu Pro Pro Ala Lys Ala Pro Ile Pro Pro Pro Arg
    2315                2320                2325
Arg Lys Arg Thr Val Val Leu Ser Glu Ser Thr Val Ser Ser Ala
2330                2335                2340
Leu Ala Glu Leu Ala Thr Lys Thr Phe Gly Ser Ser Glu Ser Ser
2345                2350                2355
Ala Val Asp Ser Gly Thr Ala Thr Ala Ser Pro Asp Gln Pro Ser
2360                2365                2370
Asp Asp Gly Asp Ala Gly Ser Asp Val Glu Ser Tyr Ser Ser Met
2375                2380                2385
Pro Pro Leu Glu Gly Glu Pro Gly Asp Pro Asp Leu Ser Asp Gly
2390                2395                2400
Ser Trp Ser Thr Val Ser Glu Glu Ala Ser Glu Asp Val Val Cys
2405                2410                2415
Cys Ser Met Ser Tyr Thr Trp Thr Gly Ala Leu Ile Thr Pro Cys
2420                2425                2430
Ala Ala Glu Glu Thr Lys Leu Pro Ile Asn Ala Leu Ser Asn Ser
2435                2440                2445
Leu Leu Arg His His Asn Leu Val Tyr Ala Thr Thr Ser Arg Ser
2450                2455                2460
Ala Ser Leu Arg Gln Lys Lys Val Thr Phe Asp Arg Leu Gln Val
2465                2470                2475
Leu Asp Asp His Tyr Arg Asp Val Leu Lys Glu Met Lys Ala Lys
2480                2485                2490
Ala Ser Thr Val Lys Ala Lys Leu Leu Ser Val Glu Glu Ala Cys
2495                2500                2505
Lys Leu Thr Pro Pro His Ser Ala Arg Ser Lys Phe Gly Tyr Gly
2510                2515                2520
Ala Lys Asp Val Arg Asn Leu Ser Ser Lys Ala Val Asn His Ile
2525                2530                2535
Arg Ser Val Trp Lys Asp Leu Leu Glu Asp Thr Glu Thr Pro Ile
2540                2545                2550
Asp Thr Thr Ile Met Ala Lys Asn Glu Val Phe Cys Val Gln Pro
2555                2560                2565
Glu Lys Gly Gly Arg Lys Pro Ala Arg Leu Ile Val Phe Pro Asp
2570                2575                2580
Leu Gly Val Arg Val Cys Glu Lys Met Ala Leu Tyr Asp Val Val
2585                2590                2595
Ser Thr Leu Pro Gln Ala Val Met Gly Ser Ser Tyr Gly Phe Gln
2600                2605                2610
Tyr Ser Pro Gly Gln Arg Val Glu Phe Leu Val Asn Ala Trp Lys
2615                2620                2625
Ala Lys Lys Cys Pro Met Gly Phe Ala Tyr Asp Thr Arg Cys Phe
2630                2635                2640
Asp Ser Thr Val Thr Glu Asn Asp Ile Arg Val Glu Glu Ser Ile
2645                2650                2655
Tyr Gln Cys Cys Asp Leu Ala Pro Glu Ala Arg Gln Ala Ile Arg
2660                2665                2670
Ser Leu Thr Glu Arg Leu Tyr Ile Gly Gly Pro Leu Thr Asn Ser
2675                2680                2685
Lys Gly Gln Asn Cys Gly Tyr Arg Arg Cys Arg Ala Ser Gly Val
2690                2695                2700
```

```
Leu Thr Thr Ser Cys Gly Asn Thr Leu Thr Cys Tyr Leu Lys Ala
    2705                2710                2715

Ala Ala Ala Cys Arg Ala Ala Lys Leu Gln Asp Cys Thr Met Leu
    2720                2725                2730

Val Cys Gly Asp Asp Leu Val Val Ile Cys Glu Ser Ala Gly Thr
    2735                2740                2745

Gln Glu Asp Glu Ala Ser Leu Arg Ala Phe Thr Glu Ala Met Thr
    2750                2755                2760

Arg Tyr Ser Ala Pro Pro Gly Asp Pro Pro Lys Pro Glu Tyr Asp
    2765                2770                2775

Leu Glu Leu Ile Thr Ser Cys Ser Ser Asn Val Ser Val Ala His
    2780                2785                2790

Asp Ala Ser Gly Lys Arg Val Tyr Tyr Leu Thr Arg Asp Pro Thr
    2795                2800                2805

Thr Pro Leu Ala Arg Ala Ala Trp Glu Thr Ala Arg His Thr Pro
    2810                2815                2820

Val Asn Ser Trp Leu Gly Asn Ile Ile Met Tyr Ala Pro Thr Leu
    2825                2830                2835

Trp Ala Arg Met Ile Leu Met Thr His Phe Phe Ser Ile Leu Leu
    2840                2845                2850

Ala Gln Glu Gln Leu Glu Lys Ala Leu Asp Cys Gln Ile Tyr Gly
    2855                2860                2865

Ala Cys Tyr Ser Ile Glu Pro Leu Asp Leu Pro Gln Ile Ile Gln
    2870                2875                2880

Arg Leu His Gly Leu Ser Ala Phe Ser Leu His Ser Tyr Ser Pro
    2885                2890                2895

Gly Glu Ile Asn Arg Val Ala Ser Cys Leu Arg Lys Leu Gly Val
    2900                2905                2910

Pro Pro Leu Arg Val Trp Arg His Arg Ala Arg Ser Val Arg Ala
    2915                2920                2925

Arg Leu Leu Ser Gln Gly Gly Arg Ala Ala Thr Cys Gly Lys Tyr
    2930                2935                2940

Leu Phe Asn Trp Ala Val Arg Thr Lys Leu Lys Leu Thr Pro Ile
    2945                2950                2955

Pro Ala Ala Ser Gln Leu Asp Leu Ser Ser Trp Phe Val Ala Gly
    2960                2965                2970

Tyr Ser Gly Gly Asp Ile Tyr His Ser Leu Ser Arg Ala Arg Pro
    2975                2980                2985

Arg Trp Phe Met Trp Cys Leu Leu Leu Leu Ser Val Gly Val Gly
    2990                2995                3000

Ile Tyr Leu Leu Pro Asn Arg
    3005                3010

<210> SEQ ID NO 57
<211> LENGTH: 3003
<212> TYPE: PRT
<213> ORGANISM: Hepatitis C virus

<400> SEQUENCE: 57

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
```

```
             35                  40                  45
Thr Arg Lys Thr Ser Glu Arg Ser Gln Pro Arg Gly Arg Gln Pro
         50                  55                  60
Ile Pro Lys Ala Arg Arg Pro Glu Gly Arg Thr Trp Ala Gln Pro Gly
 65                  70                  75                  80
Tyr Pro Trp Pro Leu Tyr Gly Asn Glu Gly Met Gly Trp Ala Gly Trp
                 85                  90                  95
Leu Leu Ser Pro Arg Gly Ser Arg Pro Ser Trp Gly Pro Thr Asp Pro
                100                 105                 110
Arg Arg Arg Ser Arg Asn Leu Gly Lys Val Ile Asp Thr Leu Thr Cys
            115                 120                 125
Gly Phe Ala Asp Leu Met Gly Tyr Ile Pro Leu Val Gly Ala Pro Leu
    130                 135                 140
Gly Gly Ala Ala Arg Ala Leu Ala His Gly Val Arg Val Leu Glu Asp
145                 150                 155                 160
Gly Val Asn Tyr Ala Thr Gly Asn Leu Pro Gly Cys Ser Phe Ser Ile
                165                 170                 175
Phe Leu Leu Ala Leu Leu Ser Cys Leu Thr Ile Pro Ala Ser Ala Tyr
                180                 185                 190
Glu Val Arg Asn Val Ser Gly Val Tyr His Val Thr Asn Asp Cys Ser
        195                 200                 205
Asn Thr Ser Ile Val Tyr Glu Thr Ala Asp Met Ile Met His Thr Pro
210                 215                 220
Gly Cys Val Pro Cys Val Arg Glu Ala Asn Ser Ser Arg Cys Trp Ala
225                 230                 235                 240
Ala Leu Thr Pro Thr Leu Ala Ala Arg Asn Thr Ser Ile Pro Thr Thr
                245                 250                 255
Thr Ile Arg Arg His Val Asp Leu Leu Val Gly Ala Ala Leu Cys
                260                 265                 270
Ser Ala Met Tyr Val Gly Asp Leu Cys Gly Ser Val Phe Leu Val Ser
            275                 280                 285
Gln Leu Phe Thr Phe Ser Pro Arg Arg His Glu Thr Val Gln Asp Cys
    290                 295                 300
Asn Cys Ser Leu Tyr Pro Gly His Val Ser Gly His Arg Met Ala Trp
305                 310                 315                 320
Asp Met Met Met Asn Trp Ser Pro Thr Ala Ala Leu Val Ala Ser Gln
                325                 330                 335
Leu Leu Arg Ile Pro Gln Ala Val Val Asp Met Val Ala Gly Ala His
            340                 345                 350
Trp Gly Val Leu Ala Gly Leu Ala Tyr Tyr Ser Met Val Gly Asn Trp
    355                 360                 365
Ala Lys Val Leu Ile Val Met Leu Leu Phe Ala Gly Val Asp Gly Ala
    370                 375                 380
Pro Asn Ala Ile Ala Ser Ser Pro Ala Arg Gly Ala Arg Gly Ile Thr
385                 390                 395                 400
Ser Leu Phe Thr Pro Gly Ala Ser Gln Asn Val Gln Leu Ile Asn Thr
                405                 410                 415
Asn Gly Ser Trp His Ile Asn Arg Thr Ala Leu Asn Cys Asn Asp Ser
                420                 425                 430
Leu His Thr Gly Phe Leu Ala Ala Leu Phe Tyr Val Asn Lys Phe Asn
            435                 440                 445
Ser Ser Gly Cys Pro Glu Arg Met Ala Ser Cys Arg Pro Ile Asp Gln
    450                 455                 460
```

```
Phe Ala Gln Gly Trp Gly Pro Ile Thr His Val Val Pro Lys Asp Leu
465                 470                 475                 480

Asp Gln Arg Pro Tyr Cys Trp His Tyr Ala Pro Arg Pro Cys Gly Ile
            485                 490                 495

Val Arg Ala Ser Glu Val Cys Gly Pro Val Tyr Cys Phe Thr Pro Ser
        500                 505                 510

Pro Val Val Gly Thr Thr Asp Arg Ser Gly Ala Pro Thr Tyr Asn
        515                 520                 525

Trp Gly Glu Asn Glu Thr Asp Val Leu Leu Asn Asn Thr Arg Pro
530                 535                 540

Pro Gln Gly Asn Trp Phe Gly Cys Thr Trp Met Asn Ser Thr Gly Phe
545                 550                 555                 560

Thr Lys Thr Cys Gly Gly Pro Pro Cys Asn Ile Gly Gly Leu Gly Asn
                565                 570                 575

Asn Thr Leu Thr Cys Pro Thr Asp Cys Phe Arg Lys His Pro Glu Ala
            580                 585                 590

Thr Tyr Ile Lys Cys Gly Ser Gly Pro Trp Leu Thr Pro Arg Cys Leu
            595                 600                 605

Val Asn Tyr Pro Tyr Arg Leu Trp His Tyr Pro Cys Thr Val Asn Phe
610                 615                 620

Thr Ile Thr Gln Val Arg Met Tyr Val Gly Gly Val Glu His Arg Leu
625                 630                 635                 640

Glu Ala Ala Cys Asn Trp Thr Arg Gly Glu Arg Cys Asn Leu Glu Asp
                645                 650                 655

Arg Asp Arg Ala Glu Leu Ser Pro Leu Leu Leu Ser Thr Thr Glu Trp
            660                 665                 670

Gln Val Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
690                 695                 700

Ile Gly Ser Ala Val Val Ser Tyr Val Ile Lys Trp Glu Tyr Val Leu
705                 710                 715                 720

Leu Leu Phe Leu Leu Leu Ala Asp Ala Arg Val Cys Ala Cys Leu Trp
                725                 730                 735

Met Met Leu Leu Ile Ala Gln Ala Glu Ala Ala Leu Glu Asn Leu Val
            740                 745                 750

Val Leu Asn Ala Ala Ser Val Ala Gly Thr His Gly Ile Leu Ser Phe
            755                 760                 765

Leu Val Phe Phe Cys Ala Ala Trp Tyr Ile Lys Gly Arg Leu Val Pro
            770                 775                 780

Gly Ala Ala Tyr Ala Phe Tyr Gly Val Trp Pro Leu Leu Leu Leu Leu
785                 790                 795                 800

Leu Ala Leu Pro Pro Arg Ala Tyr Ala Met Asp Arg Glu Met Ala Ala
                805                 810                 815

Ser Cys Gly Gly Ala Val Phe Val Gly Leu Val Leu Leu Thr Leu Ser
            820                 825                 830

Pro His Tyr Lys Pro Leu Leu Ala Lys Leu Ile Trp Trp Leu Gln Tyr
            835                 840                 845

Leu Ile Thr Arg Ala Glu Ala His Leu Gln Val Trp Val Pro Pro Leu
850                 855                 860

Asn Val Arg Gly Gly Arg Asp Ala Ile Ile Leu Leu Thr Cys Ala Leu
865                 870                 875                 880
```

```
            His Pro Glu Leu Thr Phe Asp Ile Thr Lys His Leu Leu Ala Ile Leu
                            885                 890                 895

Gly Pro Leu Met Val Leu Gln Ala Gly Ile Thr Lys Val Pro Tyr Phe
                        900                 905                 910

Val Arg Ala Gln Gly Leu Ile Arg Val Cys Met Leu Val Arg Lys Val
                        915                 920                 925

Ala Gly Gly His Tyr Val Gln Met Ala Leu Met Lys Leu Ala Ala Leu
                    930                 935                 940

Thr Gly Thr Tyr Val Tyr Asp His Leu Thr Pro Leu Arg Asp Trp Ala
            945                 950                 955                 960

His Gln Gly Leu Arg Asp Leu Ala Val Ala Val Glu Pro Val Val Phe
                            965                 970                 975

Ser Asp Met Glu Thr Lys Val Ile Thr Trp Gly Ala Asp Thr Ala Ala
                        980                 985                 990

Cys Gly Asp Ile Ile Leu Gly Leu  Pro Val Ser Ala Arg  Arg Gly Arg
                        995                 1000                1005

Glu Ile  Leu Leu Gly Pro Ala  Asp Ser Leu Glu Gly  Gln Gly Trp
                    1010                1015                1020

Arg Leu Leu Ala Pro Ile Thr  Ala Tyr Ala Gln Gln  Thr Arg Gly
                    1025                1030                1035

Leu Leu  Gly Cys Ile Ile Thr  Ser Leu Thr Gly Arg  Asp Lys Asn
                    1040                1045                1050

Gln Val  Glu Gly Glu Val Gln  Val Val Ser Thr Ala  Thr Gln Ser
                    1055                1060                1065

Phe Leu  Ala Thr Cys Val Asn  Gly Val Cys Trp Thr  Val Phe His
                    1070                1075                1080

Gly Ala  Gly Ser Lys Thr Leu  Ala Gly Pro Lys Gly  Pro Ile Thr
                    1085                1090                1095

Gln Met  Tyr Thr Asn Val Asp  Gln Asp Leu Val Gly  Trp Gln Ala
                    1100                1105                1110

Pro Ser  Gly Ala Arg Ser Leu  Thr Pro Cys Thr Cys  Gly Ser Ser
                    1115                1120                1125

Asp Leu  Tyr Leu Val Thr Arg  His Ala Asp Val Ile  Pro Val Arg
                    1130                1135                1140

Arg Arg  Gly Asp Ser Arg Gly  Ser Leu Leu Ser Pro  Arg Pro Val
                    1145                1150                1155

Ser Tyr  Leu Lys Gly Ser Ser  Gly Gly Pro Leu Leu  Cys Pro Leu
                    1160                1165                1170

Gly His  Ala Val Gly Ile Phe  Arg Ala Ala Val Cys  Thr Arg Gly
                    1175                1180                1185

Val Ala  Lys Ala Val Asp Phe  Val Pro Val Glu Ser  Met Glu Thr
                    1190                1195                1200

Thr Met  Arg Ser Pro Val Phe  Thr Asp Asn Ser Ser  Pro Pro Ala
                    1205                1210                1215

Val Pro  Gln Thr Phe Gln Val  Ala His Leu His Ala  Pro Thr Gly
                    1220                1225                1230

Ser Gly  Lys Ser Thr Arg Val  Pro Ala Ala Tyr Ala  Ala Gln Gly
                    1235                1240                1245

Tyr Lys  Val Leu Val Leu Asn  Pro Ser Val Ala Ala  Thr Leu Gly
                    1250                1255                1260

Phe Gly  Ala Tyr Met Ser Lys  Ala His Gly Ile Asp  Pro Asn Ile
                    1265                1270                1275

Arg Thr  Gly Val Arg Thr Ile  Thr Thr Gly Ala Pro  Val Thr Tyr
```

```
                1280                  1285                  1290
Ser Thr Tyr Gly Lys Phe Leu Ala Asp Gly Gly Cys Ser Gly Gly
                1295                  1300                  1305

Ala Tyr Asp Ile Ile Ile Cys Asp Glu Cys His Ser Thr Asp Ser
                1310                  1315                  1320

Thr Ser Ile Leu Gly Ile Gly Thr Val Leu Asp Gln Ala Glu Thr
                1325                  1330                  1335

Ala Gly Ala Arg Leu Val Val Leu Ala Thr Ala Thr Pro Pro Gly
                1340                  1345                  1350

Ser Val Thr Val Pro His Pro Asn Ile Glu Glu Val Ala Leu Ser
                1355                  1360                  1365

Asn Thr Gly Glu Ile Pro Phe Tyr Gly Lys Ala Ile Pro Leu Glu
                1370                  1375                  1380

Thr Ile Lys Gly Gly Arg His Leu Ile Phe Cys His Ser Lys Lys
                1385                  1390                  1395

Lys Cys Asp Glu Leu Ala Ala Lys Leu Ser Gly Leu Gly Leu Asn
                1400                  1405                  1410

Ala Val Ala Tyr Tyr Arg Gly Leu Asp Val Ser Val Ile Pro Thr
                1415                  1420                  1425

Ser Gly Asn Val Val Val Ala Thr Asp Ala Leu Met Thr Gly
                1430                  1435                  1440

Tyr Thr Gly Asp Phe Asp Ser Val Ile Asp Cys Asn Thr Cys Val
                1445                  1450                  1455

Thr Gln Thr Val Asp Phe Ser Leu Asp Pro Thr Phe Thr Ile Glu
                1460                  1465                  1470

Thr Thr Thr Val Pro Gln Asp Ala Val Ser Arg Ser Gln Arg Arg
                1475                  1480                  1485

Gly Arg Thr Gly Arg Gly Arg Arg Gly Ile Tyr Arg Phe Val Thr
                1490                  1495                  1500

Pro Gly Glu Arg Pro Ser Gly Met Phe Asp Ser Ser Val Leu Cys
                1505                  1510                  1515

Glu Cys Tyr Asp Ala Gly Cys Ala Trp Tyr Glu Leu Thr Pro Ala
                1520                  1525                  1530

Glu Thr Ser Val Arg Leu Arg Ala Tyr Leu Asn Thr Pro Gly Leu
                1535                  1540                  1545

Pro Val Cys Gln Asp His Leu Glu Phe Trp Glu Ser Val Phe Thr
                1550                  1555                  1560

Gly Leu Thr His Ile Asp Ala His Phe Leu Ser Gln Thr Lys Gln
                1565                  1570                  1575

Ala Gly Asp Asn Phe Pro Tyr Leu Val Ala Tyr Gln Ala Thr Val
                1580                  1585                  1590

Cys Ala Arg Ala Gln Ala Pro Pro Pro Ser Trp Asp Gln Met Trp
                1595                  1600                  1605

Lys Cys Leu Ile Arg Leu Lys Pro Thr Leu His Gly Pro Thr Pro
                1610                  1615                  1620

Leu Leu Tyr Arg Leu Gly Ala Val Gln Asn Glu Val Val Leu Thr
                1625                  1630                  1635

His Pro Val Thr Lys Tyr Ile Met Ala Cys Met Ser Ala Asp Leu
                1640                  1645                  1650

Glu Ile Val Thr Ser Thr Trp Val Leu Val Gly Gly Val Leu Ala
                1655                  1660                  1665

Ala Leu Ala Ala Tyr Cys Leu Thr Ala Gly Ser Val Val Ile Val
                1670                  1675                  1680
```

```
Gly Arg Ile Ile Leu Ser Gly Lys Pro Ala Val Ile Pro Asp Arg
    1685                1690                1695

Glu Val Leu Tyr Gln Glu Phe Asp Glu Met Glu Glu Cys Ala Ser
    1700                1705                1710

His Leu Pro Tyr Ile Glu Gln Gly Met Gln Leu Ala Glu Gln Phe
    1715                1720                1725

Lys Gln Lys Ala Leu Gly Leu Leu Gln Thr Ala Thr Lys Gln Ala
    1730                1735                1740

Glu Ala Val Ala Pro Val Val Glu Ser Lys Trp Gln Ala Leu Glu
    1745                1750                1755

Thr Phe Trp Ala Lys His Met Trp Asn Phe Ile Ser Gly Ile Gln
    1760                1765                1770

Tyr Leu Ala Gly Leu Ser Thr Leu Pro Gly Asn Pro Ala Ile Ala
    1775                1780                1785

Ser Leu Met Ala Phe Thr Ala Ser Ile Thr Ser Pro Leu Thr Thr
    1790                1795                1800

Gln His Thr Leu Leu Phe Asn Ile Leu Gly Gly Trp Val Ala Ala
    1805                1810                1815

Gln Leu Ala Pro Pro Ser Ala Ala Ser Ala Phe Val Gly Ala Gly
    1820                1825                1830

Ile Ala Gly Ala Ala Val Gly Ser Ile Gly Leu Gly Lys Val Leu
    1835                1840                1845

Val Asp Ile Leu Ala Gly Tyr Gly Ala Gly Val Ala Gly Ala Leu
    1850                1855                1860

Val Ala Phe Lys Ile Met Ser Gly Glu Met Pro Ser Thr Glu Asp
    1865                1870                1875

Leu Val Asn Leu Leu Pro Ala Ile Leu Ser Pro Gly Ala Leu Val
    1880                1885                1890

Val Gly Val Val Cys Ala Ala Ile Leu Arg Arg His Val Gly Pro
    1895                1900                1905

Gly Glu Gly Ala Val Gln Trp Met Asn Arg Leu Ile Ala Phe Ala
    1910                1915                1920

Ser Arg Gly Asn His Val Ser Pro Thr His Tyr Val Pro Glu Ser
    1925                1930                1935

Asp Ala Ala Ala Arg Val Thr Gln Ile Leu Ser Ser Leu Thr Ile
    1940                1945                1950

Thr Gln Leu Leu Lys Arg Leu His Gln Trp Ile Asn Glu Asp Cys
    1955                1960                1965

Ser Thr Pro Cys Ser Gly Ser Trp Leu Arg Asp Val Trp Asp Trp
    1970                1975                1980

Ile Cys Thr Val Leu Ala Asp Phe Lys Thr Trp Leu Gln Ser Lys
    1985                1990                1995

Leu Leu Pro Arg Leu Pro Gly Val Pro Phe Leu Ser Cys Gln Arg
    2000                2005                2010

Gly Tyr Lys Gly Val Trp Arg Gly Asp Gly Ile Met His Thr Thr
    2015                2020                2025

Cys Pro Cys Gly Ala Gln Ile Thr Gly His Val Lys Asn Gly Ser
    2030                2035                2040

Met Arg Ile Val Gly Pro Lys Thr Cys Ser Asn Thr Trp His Gly
    2045                2050                2055

Thr Phe Pro Ile Asn Ala Tyr Thr Thr Gly Pro Cys Thr Pro Ser
    2060                2065                2070
```

```
Pro Ala Pro Asn Tyr Ser Arg Ala Leu Trp Arg Val Ala Ala Glu
    2075                2080                2085

Glu Tyr Val Glu Val Thr Arg Val Gly Asp Phe His Tyr Val Thr
    2090                2095                2100

Gly Ile Thr Thr Asp Asn Val Lys Cys Pro Cys Gln Val Pro Ala
    2105                2110                2115

Pro Glu Phe Phe Thr Glu Val Asp Gly Val Arg Leu His Arg Tyr
    2120                2125                2130

Ala Pro Ala Cys Lys Pro Leu Leu Arg Glu Glu Val Thr Phe Leu
    2135                2140                2145

Val Gly Leu Asn Gln Tyr Leu Val Gly Ser Gln Leu Pro Cys Glu
    2150                2155                2160

Pro Glu Pro Asp Val Thr Val Leu Thr Ser Met Leu Thr Asp Pro
    2165                2170                2175

Ser His Ile Thr Ala Glu Ala Ala Lys Arg Arg Leu Ala Arg Gly
    2180                2185                2190

Ser Pro Pro Ser Leu Ala Ser Ser Ser Ala Ser Gln Leu Ser Ala
    2195                2200                2205

Pro Ser Leu Lys Ala Thr Cys Thr Ala Cys His Asp Ser Pro Asp
    2210                2215                2220

Ala Asp Leu Ile Glu Ala Asn Leu Leu Trp Arg Gln Glu Met Gly
    2225                2230                2235

Gly Asn Ile Thr Arg Val Glu Ser Glu Asn Lys Val Val Ile Leu
    2240                2245                2250

Asp Ser Phe Asp Pro Leu His Ala Glu Glu Asp Glu Gly Glu Val
    2255                2260                2265

Ser Ile Pro Ala Glu Ile Leu Arg Lys Thr Arg Lys Phe Pro Arg
    2270                2275                2280

Ala Leu Pro Val Trp Ala Arg Pro Asp Tyr Asn Pro Pro Leu Leu
    2285                2290                2295

Glu Ser Trp Lys Asp Pro Asp Tyr Val Pro Pro Val Val His Gly
    2300                2305                2310

Cys Pro Leu Pro Pro Thr Lys Ala Pro Pro Ile Pro Pro Pro Arg
    2315                2320                2325

Arg Lys Arg Thr Val Val Leu Thr Asp Ser Thr Val Ser Ser Ala
    2330                2335                2340

Leu Ala Glu Leu Ala Thr Lys Thr Phe Gly Ser Ser Glu Ser Ser
    2345                2350                2355

Ala Val Asp Ser Gly Thr Ala Thr Ala Pro Pro Asp Gln Pro Leu
    2360                2365                2370

Asp Asp Gly Asn Thr Gly Ser Asp Ala Glu Ser Tyr Ser Ser Met
    2375                2380                2385

Pro Pro Leu Glu Gly Glu Pro Gly Asp Pro Asp Leu Ser Asp Gly
    2390                2395                2400

Ser Trp Ser Thr Val Ser Glu Glu Ala Ser Glu Asp Val Val Cys
    2405                2410                2415

Cys Ser Met Ser Tyr Thr Trp Thr Gly Ala Leu Ile Thr Pro Cys
    2420                2425                2430

Ala Ala Glu Glu Ser Lys Leu Pro Ile Asn Ala Leu Ser Asn Ser
    2435                2440                2445

Leu Leu Arg His His Asn Met Val Tyr Ala Thr Thr Ser Arg Ser
    2450                2455                2460

Ala Ser Gln Arg Gln Lys Lys Val Thr Phe Asp Arg Leu Gln Val
```

```
              2465                2470                2475
Leu Asp Asp His Tyr Arg Asp Val Leu Lys Glu Met Lys Ala Lys
        2480                2485                2490
Ala Ser Thr Val Lys Ala Lys Leu Leu Ser Ile Glu Glu Ala Cys
        2495                2500                2505
Lys Leu Thr Pro Pro His Ser Ala Lys Ser Lys Phe Gly Tyr Gly
        2510                2515                2520
Ala Lys Asp Val Arg Asn Leu Ser Ser Lys Ala Val Asn His Ile
        2525                2530                2535
Arg Ser Val Trp Gln Asp Leu Leu Glu Asp Ser Glu Thr Pro Ile
        2540                2545                2550
Asp Thr Thr Ile Met Ala Lys Asn Glu Val Phe Cys Val Gln Pro
        2555                2560                2565
Glu Lys Gly Gly Arg Lys Pro Ala Arg Leu Ile Val Phe Pro Asp
        2570                2575                2580
Leu Gly Val Arg Val Cys Glu Lys Met Ala Leu Tyr Asp Val Val
        2585                2590                2595
Ser Thr Leu Pro Gln Ala Val Met Gly Ser Ser Tyr Gly Phe Gln
        2600                2605                2610
Tyr Ser Pro Gly Gln Arg Val Glu Phe Leu Val Asn Ala Trp Lys
        2615                2620                2625
Ser Lys Lys Asn Pro Met Gly Phe Ser Tyr Asp Thr Arg Cys Phe
        2630                2635                2640
Asp Ser Thr Val Thr Glu Ser Asp Ile Arg Val Glu Glu Ser Ile
        2645                2650                2655
Tyr Gln Cys Cys Asp Leu Ala Pro Glu Ala Arg Gln Ala Ile Arg
        2660                2665                2670
Ser Leu Thr Glu Arg Leu Tyr Val Gly Gly Pro Leu Thr Asn Ser
        2675                2680                2685
Lys Gly Gln Asn Cys Gly Tyr Arg Arg Cys Arg Ala Ser Gly Val
        2690                2695                2700
Leu Thr Thr Ser Cys Gly Asn Thr Leu Thr Cys Tyr Leu Lys Ala
        2705                2710                2715
Ser Ala Ala Cys Arg Ala Ala Lys Leu Gln Asp Cys Thr Met Leu
        2720                2725                2730
Val Cys Gly Asp Asp Leu Val Val Ile Cys Glu Ser Ala Gly Thr
        2735                2740                2745
Gln Glu Asp Ala Ala Ser Leu Arg Val Phe Thr Glu Ala Met Thr
        2750                2755                2760
Arg Tyr Ser Ala Pro Pro Gly Asp Pro Pro Gln Pro Glu Tyr Asp
        2765                2770                2775
Leu Glu Leu Ile Thr Ser Cys Ser Ser Asn Val Ser Val Ala His
        2780                2785                2790
Asp Ala Ser Gly Lys Arg Val Tyr Tyr Leu Thr Arg Asp Pro Thr
        2795                2800                2805
Thr Pro Leu Ala Arg Ala Ala Trp Glu Thr Ala Arg His Thr Pro
        2810                2815                2820
Val Asn Ser Trp Leu Gly Asn Ile Ile Met Phe Ala Pro Thr Leu
        2825                2830                2835
Trp Ala Arg Met Ile Leu Met Thr His Phe Phe Ser Ile Leu Leu
        2840                2845                2850
Ala Gln Glu Gln Leu Glu Lys Ala Leu Asp Cys Gln Ile Tyr Gly
        2855                2860                2865
```

```
Ala Cys Tyr Ser Ile Glu Pro Leu Asp Leu Pro Gln Ile Ile Gln
    2870            2875                2880

Arg Leu His Gly Leu Ser Ala Phe Ser Leu His Ser Tyr Ser Pro
    2885            2890                2895

Gly Glu Ile Asn Arg Val Ala Ser Cys Leu Arg Lys Leu Gly Val
    2900            2905                2910

Pro Pro Leu Arg Ala Trp Arg His Arg Ala Arg Ser Val Arg Ala
    2915            2920                2925

Lys Leu Leu Ser Leu Gly Gly Arg Ala Ala Thr Cys Gly Arg Tyr
    2930            2935                2940

Leu Phe Asn Trp Ala Val Arg Thr Lys Leu Lys Leu Thr Pro Ile
    2945            2950                2955

Pro Ala Ala Ser Gln Leu Asp Leu Ser Gly Trp Phe Val Ala Gly
    2960            2965                2970

Tyr Ser Gly Gly Asp Ile Tyr His Ser Leu Ser Arg Ala Arg Pro
    2975            2980                2985

Arg Trp Phe Met Trp Cys Leu Leu Leu Ser Val Gly Val Gly
    2990            2995                3000

<210> SEQ ID NO 58
<211> LENGTH: 3005
<212> TYPE: PRT
<213> ORGANISM: Hepatitis C virus

<400> SEQUENCE: 58

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Met Gly Trp Ala Gly Trp
                85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
        130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
                180                 185                 190

Glu Val Arg Asn Val Ser Gly Ala Tyr His Val Thr Asn Asp Cys Ser
            195                 200                 205

Asn Ser Ser Ile Val Tyr Glu Ala Ala Asp Val Ile Met His Thr Pro
        210                 215                 220

Gly Cys Val Pro Cys Val Arg Glu Asp Asn Thr Ser Arg Cys Trp Val
```

```
            225                 230                 235                 240
Ala Leu Thr Pro Thr Leu Ala Ala Arg Asn Ala Ser Val Pro Thr Met
                245                 250                 255
Thr Ile Arg Arg His Val Asp Leu Leu Val Gly Thr Ala Ala Phe Cys
                260                 265                 270
Ser Ala Met Tyr Val Gly Asp Leu Cys Gly Ser Val Phe Leu Val Ser
                275                 280                 285
Gln Leu Phe Thr Phe Ser Pro Arg Arg His Glu Thr Val Gln Asp Cys
            290                 295                 300
Asn Cys Ser Ile Tyr Pro Gly His Ile Thr Gly His Arg Met Ala Trp
305                 310                 315                 320
Asp Met Met Met Asn Trp Ser Pro Thr Thr Ala Leu Val Val Ser Gln
                325                 330                 335
Leu Leu Arg Ile Pro Gln Val Val Met Asp Ile Val Thr Gly Ala His
                340                 345                 350
Trp Gly Val Leu Ala Gly Leu Ala Tyr Tyr Ser Met Ala Gly Asn Trp
            355                 360                 365
Ala Lys Val Leu Ile Val Leu Leu Phe Ala Gly Val Asp Gly Arg
            370                 375                 380
Thr Glu Thr Thr Gly Gly Val Ala Ala Arg Thr Thr His Gly Phe Thr
385                 390                 395                 400
Ser Leu Phe Ser Val Gly Ser Lys Gln Thr Ile Gln Leu Ile Asn Thr
                405                 410                 415
Asn Gly Ser Trp His Ile Asn Arg Thr Ala Leu Asn Cys Asn Asp Ser
            420                 425                 430
Leu Gln Thr Gly Phe Leu Ala Ala Leu Phe Tyr Val Asn Lys Phe Asn
            435                 440                 445
Ser Ser Gly Cys Pro Glu Arg Met Ala Ser Cys Arg Pro Ile Asp Lys
450                 455                 460
Phe Ala Gln Gly Trp Gly Pro Ile Ser Tyr Ala Lys Ala Ser Ser Ser
465                 470                 475                 480
Asp Gln Arg Pro Tyr Cys Trp His Tyr Ala Pro Arg Pro Cys Gly Ile
                485                 490                 495
Val Pro Ala Ser Gln Val Cys Gly Pro Val Tyr Cys Phe Thr Pro Ser
                500                 505                 510
Pro Val Val Val Gly Thr Thr Asp Arg Ser Gly Val Pro Thr Tyr Asn
                515                 520                 525
Trp Gly Glu Asn Glu Thr Asp Val Leu Ile Leu Asn Asn Thr Arg Pro
            530                 535                 540
Pro Gln Gly Asn Trp Phe Gly Cys Thr Trp Met Asn Ser Thr Gly Tyr
545                 550                 555                 560
Thr Lys Thr Cys Gly Gly Pro Pro Cys Asp Ile Gly Gly Val Gly Asn
                565                 570                 575
Asp Ser Asn Arg Leu Thr Cys Pro Thr Asp Cys Phe Arg Lys His Pro
            580                 585                 590
Glu Ala Thr Tyr Thr Lys Cys Gly Ser Gly Pro Trp Leu Thr Pro Arg
            595                 600                 605
Cys Met Val Asp Tyr Pro Tyr Arg Leu Trp His Tyr Pro Cys Thr Val
            610                 615                 620
Asn Phe Thr Ile Phe Lys Val Arg Met Tyr Val Gly Gly Val Glu His
625                 630                 635                 640
Arg Leu Asn Ala Ala Cys Asn Trp Thr Arg Gly Glu Arg Cys Asn Leu
                645                 650                 655
```

-continued

```
Glu Asp Arg Asp Arg Ser Glu Leu Ser Pro Leu Leu Leu Ser Thr Thr
            660                 665                 670

Glu Trp Gln Ile Leu Pro Cys Ser Phe Thr Thr Leu Pro Ala Leu Ser
675                 680                 685

Thr Gly Leu Ile His Leu His Gln Asn Ile Val Asp Val Gln Tyr Leu
    690                 695                 700

Tyr Gly Val Gly Ser Ala Val Val Ser Leu Ala Ile Lys Trp Glu Tyr
705                 710                 715                 720

Val Leu Leu Leu Phe Leu Phe Leu Ala Asp Ala Arg Val Cys Ala Cys
                725                 730                 735

Val Trp Met Met Met Leu Ile Val Gln Ala Glu Ala Ala Leu Glu Asn
            740                 745                 750

Leu Val Val Leu Asn Ala Ala Ser Val Ala Gly Glu His Gly Ile Leu
        755                 760                 765

Ser Phe Leu Val Phe Phe Cys Ala Ala Trp Tyr Ile Lys Gly Arg Leu
    770                 775                 780

Val Pro Gly Ala Thr Tyr Ala Phe Tyr Ser Val Trp Pro Leu Leu Leu
785                 790                 795                 800

Leu Leu Leu Ala Leu Pro Pro Arg Ala Tyr Ala Met Asp Arg Glu Thr
                805                 810                 815

Ala Ala Ser Cys Gly Gly Ala Val Phe Val Gly Leu Ala Leu Leu Thr
            820                 825                 830

Leu Ser Pro His Tyr Lys Glu Leu Leu Ala Lys Leu Ile Trp Trp Leu
        835                 840                 845

Gln Tyr Leu Ile Thr Arg Ala Glu Ala Gln Leu Gln Val Trp Val Pro
    850                 855                 860

Pro Leu Asn Val Arg Gly Gly Arg Asp Ala Ile Ile Leu Leu Thr Cys
865                 870                 875                 880

Met Val His Pro Glu Leu Ile Phe Asp Ile Thr Lys Ile Leu Leu Ala
                885                 890                 895

Ile Leu Gly Pro Leu Met Val Leu Gln Ala Ser Ile Thr Lys Met Pro
            900                 905                 910

Tyr Phe Val Arg Ala Gln Gly Leu Ile Arg Ala Cys Ala Leu Val Arg
        915                 920                 925

Lys Ala Ala Gly Gly His Tyr Val Gln Met Ala Leu Met Lys Leu Ala
    930                 935                 940

Ala Leu Thr Gly Thr Tyr Val Tyr Asp His Leu Thr Pro Leu Arg Asp
945                 950                 955                 960

Trp Ala His Ser Gly Leu Arg Asp Leu Ala Val Ala Val Glu Pro Val
                965                 970                 975

Val Phe Ser Asp Met Glu Thr Lys Ile Ile Thr Trp Gly Ala Asp Thr
            980                 985                 990

Ala Ala Cys Gly Asp Ile Ile Ser  Gly Leu Pro Val Ser  Ala Arg Arg
        995                 1000                 1005

Gly Arg  Glu Ile Leu Leu Gly  Pro Ala Asp Ser Phe  Glu Gly Gln
    1010                 1015                 1020

Gly Trp  Arg Leu Leu Ala Pro  Ile Thr Ala Tyr Ala  Gln Gln Thr
    1025                 1030                 1035

Arg Gly  Leu Leu Gly Cys Ile  Ile Thr Ser Leu Thr  Gly Arg Asp
    1040                 1045                 1050

Lys Asn  Gln Val Glu Gly Glu  Val Gln Val Val Ser  Thr Ala Thr
    1055                 1060                 1065
```

-continued

```
Gln Ser Phe Leu Ala Thr Cys Val Asn Gly Val Cys Trp Thr Val
    1070                1075                1080
Phe His Gly Ala Gly Ser Lys Thr Leu Ala Gly Pro Lys Gly Pro
    1085                1090                1095
Val Thr Gln Met Tyr Thr Asn Val Asp Gln Asp Leu Val Gly Trp
    1100                1105                1110
Gln Ala Pro Pro Gly Ala Arg Ser Leu Thr Pro Cys Thr Cys Gly
    1115                1120                1125
Ser Ser Asp Leu Tyr Leu Val Thr Arg His Ala Asp Val Ile Pro
    1130                1135                1140
Val Arg Arg Arg Gly Asp Ser Arg Gly Ser Leu Leu Ser Pro Arg
    1145                1150                1155
Pro Val Ser Tyr Leu Lys Gly Ser Ser Gly Gly Pro Leu Leu Cys
    1160                1165                1170
Ser Ser Gly His Ala Val Gly Ile Phe Arg Ala Ala Val Cys Thr
    1175                1180                1185
Arg Gly Val Ala Lys Ala Val Asp Phe Val Pro Val Glu Ser Met
    1190                1195                1200
Glu Thr Thr Met Arg Ser Pro Val Phe Thr Asp Asn Ser Ser Pro
    1205                1210                1215
Pro Ala Val Pro Gln Thr Phe Gln Val Ala His Leu His Ala Pro
    1220                1225                1230
Thr Gly Ser Gly Lys Ser Thr Lys Val Pro Ala Ala Tyr Ala Ala
    1235                1240                1245
Gln Gly Tyr Lys Val Leu Val Leu Asn Pro Ser Val Ala Ala Thr
    1250                1255                1260
Leu Ser Phe Gly Ala Tyr Met Ser Lys Ala His Gly Val Asp Pro
    1265                1270                1275
Asn Ile Arg Thr Gly Val Arg Thr Ile Thr Thr Gly Ala Pro Ile
    1280                1285                1290
Thr Tyr Ser Thr Tyr Gly Lys Phe Leu Ala Asp Gly Gly Cys Ser
    1295                1300                1305
Gly Gly Ala Tyr Asp Ile Ile Ile Cys Asp Glu Cys His Ser Ile
    1310                1315                1320
Asp Ser Thr Ser Ile Leu Gly Ile Gly Thr Val Leu Asp Gln Ala
    1325                1330                1335
Glu Thr Ala Gly Ala Arg Leu Val Val Leu Ala Thr Ala Thr Pro
    1340                1345                1350
Pro Gly Ser Val Thr Val Pro His Pro Asn Ile Glu Glu Val Ala
    1355                1360                1365
Leu Ser Asn Thr Gly Glu Ile Pro Phe Tyr Gly Lys Ala Ile Pro
    1370                1375                1380
Ile Glu Thr Ile Lys Gly Gly Arg His Leu Ile Phe Cys His Ser
    1385                1390                1395
Lys Lys Lys Cys Asp Glu Ile Ala Ala Lys Leu Ser Ser Leu Gly
    1400                1405                1410
Leu Asn Ala Val Ala Tyr Tyr Arg Gly Leu Asp Val Ser Val Ile
    1415                1420                1425
Pro Thr Ser Gly Asn Val Val Val Val Ala Thr Asp Ala Leu Met
    1430                1435                1440
Thr Gly Phe Thr Gly Asp Phe Asp Ser Val Ile Asp Cys Asn Thr
    1445                1450                1455
Cys Val Thr Gln Thr Val Asp Phe Ser Leu Asp Pro Thr Phe Thr
```

```
                1460                1465                1470

Ile  Glu  Thr  Thr  Thr  Val  Pro  Gln  Asp  Ala  Val  Ser  Arg  Ser  Gln
    1475                1480                1485

Arg  Arg  Gly  Arg  Thr  Gly  Arg  Gly  Arg  Gly  Ile  Tyr  Arg  Phe
    1490                1495                1500

Val  Thr  Pro  Gly  Glu  Arg  Pro  Ser  Gly  Met  Phe  Asp  Ser  Ser  Val
    1505                1510                1515

Leu  Cys  Glu  Cys  Tyr  Asp  Ala  Gly  Cys  Ala  Trp  Tyr  Glu  Leu  Thr
    1520                1525                1530

Pro  Ala  Glu  Thr  Ser  Val  Arg  Leu  Arg  Ala  Tyr  Leu  Asn  Thr  Pro
    1535                1540                1545

Gly  Leu  Pro  Val  Cys  Gln  Asp  His  Leu  Glu  Phe  Trp  Glu  Ser  Val
    1550                1555                1560

Phe  Thr  Gly  Leu  Thr  His  Ile  Asp  Ala  His  Phe  Leu  Ser  Gln  Thr
    1565                1570                1575

Lys  Gln  Ala  Gly  Asp  Asn  Phe  Pro  Tyr  Leu  Val  Ala  Tyr  Gln  Ala
    1580                1585                1590

Thr  Val  Cys  Ala  Arg  Ala  Gln  Ala  Pro  Pro  Pro  Ser  Trp  Asp  Gln
    1595                1600                1605

Met  Trp  Lys  Cys  Leu  Ile  Arg  Leu  Lys  Pro  Thr  Leu  His  Gly  Pro
    1610                1615                1620

Thr  Pro  Leu  Leu  Tyr  Arg  Leu  Gly  Ala  Val  Gln  Asn  Glu  Val  Ile
    1625                1630                1635

Leu  Thr  His  Pro  Ile  Thr  Lys  Tyr  Ile  Met  Ala  Cys  Met  Ala  Ala
    1640                1645                1650

Asp  Leu  Glu  Val  Val  Thr  Ser  Thr  Trp  Val  Leu  Val  Gly  Gly  Val
    1655                1660                1665

Leu  Ala  Ala  Leu  Ala  Ala  Tyr  Cys  Leu  Thr  Thr  Gly  Ser  Val  Val
    1670                1675                1680

Ile  Val  Gly  Arg  Ile  Ile  Leu  Ser  Gly  Lys  Pro  Ala  Val  Ile  Pro
    1685                1690                1695

Asp  Arg  Glu  Val  Leu  Tyr  Arg  Glu  Phe  Asp  Glu  Met  Glu  Glu  Cys
    1700                1705                1710

Ala  Ser  His  Leu  Pro  Tyr  Ile  Glu  Gln  Gly  Met  Gln  Leu  Ala  Glu
    1715                1720                1725

Gln  Phe  Lys  Gln  Lys  Ala  Leu  Gly  Leu  Leu  Gln  Thr  Ala  Thr  Lys
    1730                1735                1740

Gln  Ala  Glu  Ala  Ala  Ala  Pro  Val  Val  Glu  Ser  Lys  Trp  Arg  Ala
    1745                1750                1755

Leu  Glu  Thr  Phe  Trp  Ala  Lys  His  Met  Trp  Asn  Phe  Ile  Ser  Gly
    1760                1765                1770

Ile  Gln  Tyr  Leu  Ala  Gly  Leu  Ser  Thr  Leu  Pro  Gly  Asn  Pro  Ala
    1775                1780                1785

Ile  Ala  Ser  Leu  Met  Ala  Phe  Thr  Ala  Ser  Ile  Thr  Ser  Pro  Leu
    1790                1795                1800

Thr  Thr  Gln  His  Thr  Leu  Leu  Phe  Asn  Ile  Leu  Gly  Gly  Trp  Val
    1805                1810                1815

Ala  Ala  Gln  Leu  Ala  Pro  Pro  Ser  Ala  Ala  Ser  Ala  Phe  Val  Gly
    1820                1825                1830

Ala  Gly  Ile  Ala  Gly  Ala  Ala  Val  Gly  Ser  Ile  Gly  Leu  Gly  Lys
    1835                1840                1845

Val  Leu  Val  Asp  Ile  Leu  Ala  Gly  Tyr  Gly  Ala  Gly  Val  Ala  Gly
    1850                1855                1860
```

```
Ala Leu Val Ala Phe Lys Val Met Ser Gly Glu Met Pro Ser Thr
        1865                1870                1875

Glu Asp Leu Val Asn Leu Leu Pro Ala Ile Leu Ser Pro Gly Ala
        1880                1885                1890

Leu Val Val Gly Val Val Cys Ala Ala Ile Leu Arg Arg His Val
        1895                1900                1905

Gly Pro Gly Glu Gly Ala Val Gln Trp Met Asn Arg Leu Ile Ala
        1910                1915                1920

Phe Ala Ser Arg Gly Asn His Val Ser Pro Thr His Tyr Val Pro
        1925                1930                1935

Glu Ser Asp Ala Ala Arg Val Thr Gln Ile Leu Ser Ser Leu
        1940                1945                1950

Thr Ile Thr Gln Leu Leu Lys Arg Leu His Gln Trp Ile Asn Glu
        1955                1960                1965

Asp Cys Ser Thr Pro Cys Ser Gly Ser Trp Leu Arg Asp Val Trp
        1970                1975                1980

Asp Trp Ile Cys Thr Val Leu Thr Asp Phe Lys Thr Trp Leu Gln
        1985                1990                1995

Ser Lys Leu Leu Pro Arg Leu Pro Gly Val Pro Phe Phe Ser Cys
        2000                2005                2010

Gln Arg Gly Tyr Lys Gly Val Trp Arg Gly Asp Gly Ile Met Gln
        2015                2020                2025

Thr Thr Cys Pro Cys Gly Ala Gln Ile Thr Gly His Val Lys Asn
        2030                2035                2040

Gly Ser Met Arg Ile Ile Gly Pro Lys Thr Cys Ser Asn Thr Trp
        2045                2050                2055

His Gly Thr Phe Pro Ile Asn Ala Tyr Thr Thr Gly Pro Cys Thr
        2060                2065                2070

Pro Ser Pro Ala Pro Asn Tyr Ser Arg Ala Leu Trp Arg Val Ala
        2075                2080                2085

Ala Glu Glu Tyr Val Glu Val Thr Arg Val Gly Asp Phe His Tyr
        2090                2095                2100

Val Thr Gly Met Thr Thr Asp Asn Leu Lys Cys Pro Cys Gln Val
        2105                2110                2115

Pro Ala Pro Glu Phe Tyr Thr Glu Val Asp Gly Val Arg Leu His
        2120                2125                2130

Arg Tyr Ala Pro Ala Cys Lys Pro Leu Leu Arg Glu Glu Val Thr
        2135                2140                2145

Phe Leu Val Gly Leu Asn Glu Tyr Pro Val Gly Ser Gln Leu Pro
        2150                2155                2160

Cys Glu Pro Glu Pro Asp Val Thr Val Leu Ala Ser Met Leu Thr
        2165                2170                2175

Asp Pro Ser His Ile Thr Ala Glu Thr Ala Lys Arg Arg Leu Ala
        2180                2185                2190

Arg Gly Ser Pro Pro Ser Leu Ala Ser Ser Ser Ala Ser Gln Leu
        2195                2200                2205

Ser Ala Pro Ser Leu Lys Ala Thr Cys Thr Thr Asn His Asp Ser
        2210                2215                2220

Pro Asp Ala Asp Leu Ile Glu Ala Asn Leu Leu Trp Arg Gln Glu
        2225                2230                2235

Met Gly Gly Asn Ile Thr Arg Val Glu Ser Glu Asn Lys Val Val
        2240                2245                2250
```

```
Ile Leu Asp Ser Phe Asp Pro Leu Arg Ala Glu Glu Asp Glu Arg
2255                2260                2265

Glu Val Ser Ile Pro Ala Glu Ile Leu Arg Lys Ser Lys Lys Phe
2270                2275                2280

Pro Ser Ala Met Pro Val Trp Ala Arg Pro Asp Tyr Asn Pro Pro
2285                2290                2295

Leu Leu Glu Ser Trp Lys Ser Pro Asp Tyr Val Pro Pro Val Val
2300                2305                2310

His Gly Cys Pro Leu Pro Pro Ala Lys Ala Pro Pro Val Pro Pro
2315                2320                2325

Pro Arg Arg Lys Arg Thr Val Val Leu Thr Glu Ser Thr Val Ser
2330                2335                2340

Ser Ala Leu Ala Glu Leu Ala Thr Lys Thr Phe Ser Ser Ser Glu
2345                2350                2355

Ser Ser Ala Val Asp Ser Gly Thr Ala Thr Ala Pro Pro Asp Gln
2360                2365                2370

Pro Leu Asp Asp Gly Asp Ala Gly Ser Asp Ala Gly Ser Tyr Ser
2375                2380                2385

Ser Met Pro Pro Leu Glu Gly Glu Pro Gly Asp Pro Asp Leu Ser
2390                2395                2400

Asp Gly Ser Trp Ser Thr Val Ser Glu Glu Ala Ser Glu Asp Val
2405                2410                2415

Val Cys Cys Ser Met Ser Tyr Thr Trp Thr Gly Ala Leu Ile Thr
2420                2425                2430

Pro Cys Ala Ala Glu Glu Ser Lys Leu Pro Ile Asn Ala Leu Ser
2435                2440                2445

Asn Ser Leu Leu Arg His His Asn Met Val Tyr Ala Thr Thr Ser
2450                2455                2460

Arg Ser Ala Ser Gln Arg Gln Lys Lys Val Thr Phe Asp Arg Leu
2465                2470                2475

Gln Val Leu Asp Asp His Tyr Arg Asp Val Leu Lys Glu Met Lys
2480                2485                2490

Ala Lys Ala Ser Thr Val Lys Ala Lys Leu Leu Ser Val Glu Glu
2495                2500                2505

Ala Cys Lys Leu Thr Pro Pro His Ser Ala Arg Ser Lys Phe Gly
2510                2515                2520

Tyr Gly Ala Lys Asp Val Arg Asn Leu Ser Ser Lys Ala Val Asn
2525                2530                2535

His Ile His Ser Val Trp Lys Asp Leu Leu Glu Asp Ser Glu Thr
2540                2545                2550

Pro Ile Asp Thr Thr Ile Met Ala Lys Asn Glu Val Phe Cys Val
2555                2560                2565

Gln Pro Glu Lys Gly Gly Arg Lys Pro Ala Arg Leu Ile Val Tyr
2570                2575                2580

Pro Asp Leu Gly Val Arg Val Cys Glu Lys Met Ala Leu Tyr Asp
2585                2590                2595

Val Val Ser Thr Leu Pro Gln Ala Val Met Gly Ser Ser Tyr Gly
2600                2605                2610

Phe Gln Tyr Ser Pro Gly Gln Arg Val Glu Phe Leu Val Asn Ala
2615                2620                2625

Trp Lys Ser Lys Lys Cys Pro Met Gly Phe Ala Tyr Asp Thr Arg
2630                2635                2640

Cys Phe Asp Ser Thr Val Thr Glu Ser Asp Ile Arg Val Glu Glu
```

-continued

```
              2645                2650                2655

Ser Ile Tyr Gln Cys Cys Asp Leu Ala Pro Glu Ala Arg Gln Ala
            2660                2665                2670

Ile Arg Ser Leu Thr Glu Arg Leu Tyr Val Gly Gly Pro Leu Thr
            2675                2680                2685

Asn Ser Lys Gly Gln Asn Cys Gly Tyr Arg Arg Cys Arg Ala Ser
            2690                2695                2700

Gly Val Leu Thr Thr Ser Cys Gly Asn Thr Leu Thr Cys Tyr Leu
            2705                2710                2715

Lys Ala Ser Ala Ala Cys Arg Ala Ala Lys Leu Gln Asp Cys Thr
            2720                2725                2730

Met Leu Val Cys Gly Asp Asp Leu Val Val Ile Cys Glu Ser Ala
            2735                2740                2745

Gly Thr Gln Glu Asp Ala Ala Ser Leu Arg Val Phe Thr Glu Ala
            2750                2755                2760

Met Thr Arg Tyr Ser Ala Pro Pro Gly Asp Pro Pro Gln Pro Glu
            2765                2770                2775

Tyr Asp Leu Glu Leu Ile Thr Ser Cys Ser Ser Asn Val Ser Val
            2780                2785                2790

Ala His Asp Ala Ser Gly Lys Arg Val Tyr Tyr Leu Thr Arg Asp
            2795                2800                2805

Pro Thr Thr Pro Leu Ala Arg Ala Ala Trp Glu Thr Ala Lys His
            2810                2815                2820

Thr Pro Val Asn Ser Trp Leu Gly Asn Ile Ile Met Tyr Ala Pro
            2825                2830                2835

Thr Leu Trp Ala Arg Met Ile Leu Met Thr His Phe Phe Ser Ile
            2840                2845                2850

Leu Leu Ala Gln Glu Gln Leu Glu Lys Ala Leu Asp Cys Gln Ile
            2855                2860                2865

Tyr Gly Ala Cys Tyr Ser Ile Glu Pro Leu Asp Leu Pro Gln Ile
            2870                2875                2880

Ile Gln Arg Leu His Gly Leu Ser Ala Phe Ser Leu His Ser Tyr
            2885                2890                2895

Ser Pro Gly Glu Ile Asn Arg Val Ala Ser Cys Leu Arg Lys Leu
            2900                2905                2910

Gly Val Pro Pro Leu Arg Thr Trp Arg His Arg Ala Arg Ser Val
            2915                2920                2925

Arg Ala Lys Leu Leu Ser Gln Gly Gly Arg Ala Ala Ile Cys Gly
            2930                2935                2940

Lys Tyr Leu Phe Asn Trp Ala Val Arg Thr Lys Leu Lys Leu Thr
            2945                2950                2955

Pro Ile Pro Ala Ala Ser Arg Leu Asp Leu Ser Gly Trp Phe Val
            2960                2965                2970

Ala Gly Tyr Gly Gly Gly Asp Ile Tyr His Ser Val Ser Arg Ala
            2975                2980                2985

Arg Pro Arg Trp Phe Met Trp Cys Leu Leu Leu Leu Ser Val Gly
            2990                2995                3000

Val Gly
            3005
```

NEAR FULL-GENOME ASSAY OF HCV DRUG RESISTANCE

CROSS-REFERENCE TO RELATED APPLICATIONS

This application is the National Stage of International Application No. PCT/IB2008/002924, filed Oct. 31, 2008, which claims the benefit of International Application No. PCT/IB2007/003304, filed Oct. 31, 2007, the contents of which are incorporated by reference herein.

BACKGROUND OF THE INVENTION

1. Field of the Invention

The present invention relates to assays that detect and characterize single or linked mutations in a genome of a Hepatitis C Virus (HCV) that are associated with resistance of a subject to an anti-HCV drug. The assays can also be used for predicting resistance to an anti-HCV drug of a subject infected with HCV prior to or early during antiviral therapy or for selecting an alternative therapy for an HCV-infected subject that has developed resistance to a particular therapeutic drug or drug combination. The invention also relates to nucleotide primer pairs and kits for carrying out these assays.

2. Description of Related Art

HCV was cloned and characterized about 15 years ago by Choo and colleagues. Choo et al. (1989) Science 244, 359-362. HCV belongs to the family of Flaviviridae and comprises an enveloped nucleocapsid and a single-stranded RNA genome of positive polarity. (Bartenschlager et al. (2003) Antiviral Res 60, 91-102.) The HCV genome consists of 5' and 3' noncoding (UTR or NCR) regions that flank a single long open reading frame (ORF). This ORF encodes three structural proteins at the amino-terminal end and six non-structural (NS) proteins at the carboxy-terminal end. The structural proteins are the nucleocapsid core protein (C) and the two glycoproteins envelope 1 (E1) and envelope 2 (E2). The non-structural proteins are named NS2, NS3, NS4a, NS4b, NS5a, NS5b. The 5'NCR is the most highly conserved region of the HCV genome, whereas the sequences of the two envelope proteins (E1 and E2) are highly variable among different HCV isolates. The highest degree of variation has been observed in a region within E2, now commonly termed hypervariable region 1.

Since the initial identification of HCV, at least 7 different major viral types have been identified and designated genotype 1 through 7. Within these genotypes are numerous subtypes (e.g. HCV1a, 1b, 1c). Genotype and subtype of a virus with which a subject is infected may affect clinical prognosis as well as responsiveness to various drug treatments. (Simmonds et al. (1995) Hepatology 21, 570-582; Bukh et al. (1995) Semin Liver Dis 15, 41-63; Chevaliez and Pawlotsky (2007) World J Gastroenterol 13, 2461-2466).

HCV infection remains a serious medical problem to this date. There are currently about 170 million people infected with HCV. HCV is transmitted primarily by blood and blood products as well as by vertical transmission during pregnancy. The initial course of infection is typically mild. However, the immune system is often incapable of clearing the virus, and subjects with persistent infection are at a high risk for liver cirrhosis and hepatocellular carcinoma. (Poynard et al. (1997) Lancet 349, 825-832).

Current standard treatment for chronic HCV infection is based on a combination of pegylated interferon alpha and ribavirin. This therapy produces a sustained anti-viral response in 85-90% of subjects infected with genotypes 2 and 3, but, unfortunately, only in about 45% of subjects infected with the prevalent genotype 1. (Stribling et al. (2006) Gastroenterol Clin North Am vol, 463-486.) Additional therapies using other drugs and drug combinations that are endowed with higher antiviral activity and superior safety profiles are clearly required, in particular for the prevention of HCV recurrence.

Introduction of diagnostic tests for screening blood products has significantly reduced the rate of new infection. Availability of in vitro models, i.e., HCV subgenomic replicon models and an infectious cell culture model, and improvements in molecular research techniques such as the Polymerase Chain Reaction (PCR) have facilitated development of additional potent inhibitors of HCV replication targeting directly a viral protein or acting indirectly through host proteins involved in viral infection. (Bartenschlager (2002) Nat Rev Drug Discov 1, 911-916; Wakita et al. (2005) Nat Med 11, 791-796.) Several of these new compounds have entered clinical trials or are already on the market (http://www.hcvadvocate.org/hepatitis/hepC/HCVDrugs_2007.pdf).

Assays have been developed that are aimed at providing prognostic information about the likelihood of responsiveness to an anti-HCV therapy. (Gretch et al. (1997) Hepatology 26, 43s-47s; Podzorski (2002) Arch Pathol Lab Med 126, 285-290). These assays include serological tests and qualitative or quantitative molecular tests. Examples of PCR-based assays of HCV viral load are Cobas Amplicor® (Roche) and m2000 Real-Time PCR Diagnostics System® (Abott). Other PCR-based assays that include, e.g., Versant® HCV Genotyping Assay (Bayer Diagnostics), INNO-LiPA HCV II® (Innogenetics), GEN-ETI-K DEIA kit (Sorin, Saluggia, Italy) and TRUGENE HCV 5'NC genotyping kit (Visible Genetics Europe, Evry, France) identify HCV genotype and subtype. Systematic assessment of HCV genotype prior to therapy has been advocated recently because HCV genotype will determine choice and dose regimen of the most effective anti-HCV drug, e.g. ribavirin or interferon, as well as duration of treatment. Current genotype identification relies primarily on sequencing of a small subregion of an HCV genome, e.g., the 5'UTR, but not of a full or nearly full HCV genome.

SUMMARY OF THE INVENTION

In its most general embodiment, the present invention relates to an assay for identifying a mutation in the genome of an HCV present in a sample. The assay comprises the following steps that are carried out in sequence:
  a) extraction of viral RNA from the sample containing the HCV;
  b) determination of genotype and subtype of the HCV;
  c) synthesis of partial cDNAs of the genome of the HCV in three separate reverse transcription reactions, the first reverse transcription reaction initiated from a first outer antisense primer selected to specifically hybridize to a sequence in the 3'UTR of a prototype HCV genome of the same genotype and subtype, the second reverse transcription reaction initiated from a second outer antisense primer selected to specifically hybridize to a sequence in the NS4B-NS5A region of the genome of the prototype HCV and the third reverse transcription reaction initiated from a third outer antisense primer selected to specifically hybridize to a sequence in the NS2 region of the genome of the prototype HCV;
  d) second strand synthesis and amplification of the partial cDNAs of step c) in three separate PCR reactions, the first PCR reaction comprising an aliquot of the first reverse transcription reaction, the first outer antisense primer and a first outer sense primer selected to specifically hybridize to a complementary sequence in the NS4B-NS5A region of the genome of the prototype HCV, the second PCR reaction comprising an aliquot of the second reverse transcription reaction, the second outer antisense primer and a second outer sense primer selected to specifically hybridize to a complementary sequence in the NS2 region of the genome of the prototype HCV, and the third PCR reaction comprising an aliquot of the third reverse transcription reaction, the third outer antisense primer and a third outer sense primer selected to specifically hybridize to a complementary sequence in the 5'UTR region of the genome of the prototype HCV, wherein the second outer antisense primer hybridizes to a sequence in the NS4B-NS5A region of the genome of the prototype HCV that is located 3' to the region that is complementary to the first outer sense primer and wherein the third outer antisense primer hybridizes to a sequence in the NS2 region of the genome of the prototype HCV that is located 3' to the region that is complementary to the second outer sense primer;

e) further amplification of the partial cDNAs of step d) in three separate nested PCR reactions, the first nested PCR reaction comprising an aliquot of the first PCR reaction and first inner antisense and sense primers, the second nested PCR reaction comprising an aliquot of the second PCR reaction and second inner antisense and sense primers, and the third nested PCR reaction comprising an aliquot of the third PCR reaction and third inner antisense and sense primers, wherein the inner primers do not overlap the outer primers, the second inner antisense primer hybridizes to a sequence in the NS4B-NS5A region of the genome of the prototype HCV that is located 3' to the region that is complementary to the first inner sense primer and the third inner antisense primer hybridizes to a sequence in the NS2 region of the genome of the prototype HCV that is located 3' to the region that is complementary to the second inner sense primer;

f) sequence analysis of the further amplified cDNAs of step e); and g) comparison of the sequences obtained from step f) with that of the prototype HCV.

In an another embodiment, an assay of the invention is used to identify and characterize individual and linked mutations associated with resistance of an HCV-infected subject to particular anti-HCV drugs or drug combinations and to generate or expand a data bank of HCV mutations associated with anti-HCV drug resistance. The assay entails the following steps that are carried out in sequence:

a) extraction of viral RNA from a sample taken from a subject carrying an HCV that is resistant to an anti-HCV drug or drug combination with which the subject has been treated as indicated by treatment failure;

b) determination of genotype and subtype of the HCV;

c) synthesis of partial cDNAs of the genome of the HCV in three separate reverse transcription reactions, the first reverse transcription reaction initiated from a first outer antisense primer selected to specifically hybridize to a sequence in the 3'UTR of a prototype HCV genome of the same genotype and subtype, the second reverse transcription reaction initiated from a second outer antisense primer selected to specifically hybridize to a sequence in the NS4B-NS5A region of the genome of the prototype HCV and the third reverse transcription reaction initiated from a third outer antisense primer selected to specifically hybridize to a sequence in the NS2 region of the genome of the prototype HCV;

d) second strand synthesis and amplification of the partial cDNAs of step c) in three separate PCR reactions, the first PCR reaction comprising an aliquot of the first reverse transcription reaction, the first outer antisense primer and a first outer sense primer selected to specifically hybridize to a complementary sequence in the NS4B-NS5A region of the genome of the prototype HCV, the second PCR reaction comprising an aliquot of the second reverse transcription reaction, the second outer antisense primer and a second outer sense primer selected to specifically hybridize to a complementary sequence in the NS2 region of the genome of the prototype HCV, and the third PCR reaction comprising an aliquot of the third reverse transcription reaction, the third outer antisense primer and a third outer sense primer selected to specifically hybridize to a complementary sequence in the 5'UTR region of the genome of the prototype HCV, wherein the second outer antisense primer hybridizes to a sequence in the NS4B-NS5A region of the genome of the prototype HCV that is located 3' to the region that is complementary to the first outer sense primer and wherein the third outer antisense primer hybridizes to a sequence in the NS2 region of the genome of the prototype HCV that is located 3' to the region that is complementary to the second outer sense primer;

e) further amplification of the partial cDNAs of step d) in three separate nested PCR reactions, the first nested PCR reaction comprising an aliquot of the first PCR reaction and first inner antisense and sense primers, the second nested PCR reaction comprising an aliquot of the second PCR reaction and second inner antisense and sense primers, and the third nested PCR reaction comprising an aliquot of the third PCR reaction and third inner antisense and sense primers, wherein the inner primers do not overlap the outer primers, the second inner antisense primer hybridizes to a sequence in the NS4B-NS5A region of the genome of the prototype HCV that is located 3' to the region that is complementary to the first inner sense primer and the third inner antisense primer hybridizes to a sequence in the NS2 region of the genome of the prototype HCV that is located 3' to the region that is complementary to the second inner sense primer;

f) sequence analysis of the further amplified cDNAs of step e);

g) comparison of the sequences obtained from step f) with that of the prototype HCV and identification of mutations; and h) entry of the mutations identified in a data bank of HCV mutations associated with anti-HCV drug resistance.

In a related embodiment, an assay of the invention is employed to identify and characterize individual and linked mutations associated with resistance of an HCV-infected subject to the treatment administered and, making use of a data bank of HCV mutations associated with anti-HCV drug resistance to select an alternative anti-HCV drug or drug combination to which the virus variant of the subject is not expected to be resistant for further therapy of the subject. The assay comprises the same steps as that of the preceding embodiment, except for step h) that is replaced by a step entailing a search of a data bank of HCV mutations associated with anti-HCV drug resistance for the mutations identified and selection for subsequent treatment of the subject of an anti-HCV drug or drug combination to which the HCV is not expected to be resistant.

In another embodiment, the assay of the preceding embodiment is employed for analysing a sample taken from a subject infected with HCV prior to commencement of any pharmacological therapy of the subject. Information obtained from this analysis will permit a treating physician to select an anti-HCV drug or drug combination for treatment of the subject, to which anti-HCV drug or drug combination the HCV variant or variants present in the subject are not expected to be resistant.

A more specific embodiment of the invention relates to an assay for identifying a mutation in the genome of an HCV1b present in a sample. The assay comprises the following steps that are carried out in sequence:

a) extraction of viral RNA from the sample containing the HCV;
b) determination of genotype and subtype of the HCV;
c) provided that step b) indicated that the HCV is of type 1b, synthesis of partial cDNAs of the genome of the HCV in three separate reverse transcription reactions, the first reverse transcription reaction initiated from primer poly-A, the second reverse transcription reaction initiated from primer HCV1bOR6312 and the third reverse transcription reaction initiated from primer HCV1bOR3306;
d) second strand synthesis and amplification of the partial cDNAs of step c) in three separate PCR reactions, the first PCR reaction comprising an aliquot of the first reverse transcription reaction and primer pair poly-A/HCV1bOF6074, the second PCR reaction comprising an aliquot of the second reverse transcription reaction and primer pair HCV1bOR6312/HCV1bOF1977 and the third PCR reaction comprising an aliquot of the third reverse transcription reaction and primer pair HCV1bOR3306/HCVOF129;
e) further amplification of the partial cDNAs of step d) in three separate nested PCR reactions, the first nested PCR reaction comprising an aliquot of the first PCR reaction and primer pair HCV1bIR9339/HCV1bIF6126, the second nested PCR reaction comprising an aliquot of the second PCR reaction and primer pair HCV1bIR6282/HCV1bIF2523, and the third nested PCR reaction comprising an aliquot of the third PCR reaction and primer pair HCV1bIR2770/HCVIF278;
f) sequence analysis of the further amplified cDNAs of step e); and
g) comparison of the sequences obtained from step f) with that of a prototype HCV1b.

In another embodiment, an assay of the invention is used to identify and characterize individual and linked mutations associated with resistance of a subject infected with an HCV 1b to a particular anti-HCV drug or drug combination and to generate or expand a data bank of HCV mutations associated with anti-HCV drug resistance. The assay entails the following steps that are carried out in sequence:

a) extraction of viral RNA from a sample taken from a subject harboring an HCV that is resistant to an anti-HCV drug or drug combination with which the subject has been treated;
b) determination of genotype and subtype of the HCV;
c) provided that step b) indicated that the HCV is of type 1b, synthesis of partial cDNAs of the genome of the HCV in three separate reverse transcription reactions, the first reverse transcription reaction initiated from primer poly-A, the second reverse transcription reaction initiated from primer HCV1bOR6312 and the third reverse transcription reaction initiated from primer HCV1bOR3306;
d) second strand synthesis and amplification of the partial cDNAs of step c) in three separate PCR reactions, the first PCR reaction comprising an aliquot of the first reverse transcription reaction and primer pair poly-A/HCV1bOF6074, the second PCR reaction comprising an aliquot of the second reverse transcription reaction and primer pair HCV1bOR6312/HCV1bOF1977 and the third PCR reaction comprising an aliquot of the third reverse transcription reaction and primer pair HCV1bOR3306/HCVOF129;
e) further amplification of the partial cDNAs of step d) in three separate nested PCR reactions, the first nested PCR reaction comprising an aliquot of the first PCR reaction and primer pair HCV1bIR9339/HCV1bIF6126, the second nested PCR reaction comprising an aliquot of the second PCR reaction and primer pair HCV1bIR6282/HCV1bIF2523, and the third nested PCR reaction comprising an aliquot of the third PCR reaction and primer pair HCV1bIR2770/HCV1F278;
f) sequence analysis of the further amplified cDNAs of step e);
g) comparison of the sequences obtained from step f) with that of a prototype HCV1b and identification of mutations; and
h) entry of the mutations identified in a data bank of HCV mutations associated with anti-HCV drug resistance.

Once a useful data bank has been assembled, a similar assay can be utilized to analyze samples from treatment-naïve HCV1b-infected subjects or from subjects infected with HCV1b that have been treated and developed resistance to the treatment regimen to select an appropriate anti-HCV drug or drug combination for treatment or further treatment, respectively. In such embodiments, step h) of the assay described immediately above is replaced by a step entailing a search of a data bank of HCV mutations associated with anti-HCV drug resistance for the mutations identified and selection for subsequent treatment of the subject of an anti-HCV drug or drug combination to which the HCV is not expected to be resistant.

The invention also relates to primer pairs consisting of poly-A and HCV1bOF6074, HCV1bOR6312 and HCV1bOF1977, HCV1bOR3306 and HCVOF129, HCV1bIR9339 and HCV1bIF6126, HCV1bIR6282 and HCV1bIF2523, and HCV1bIR2770 and HCVIF278. Kits for detecting mutations in an HCV genome are also an object of the invention. These kits comprise at least one or all of the aforementioned primer pairs and can include additional reagents such as e.g., polymerase, buffers, and nucleoside triphosphates.

BRIEF DESCRIPTION OF THE DRAWINGS

FIGS. 3a and b compare translated HCV amino acid sequences from two infected subjects obtained by an assay of the invention with the sequence of a prototype HCV genome.

DETAILED DESCRIPTION OF THE INVENTION

Figure 1:
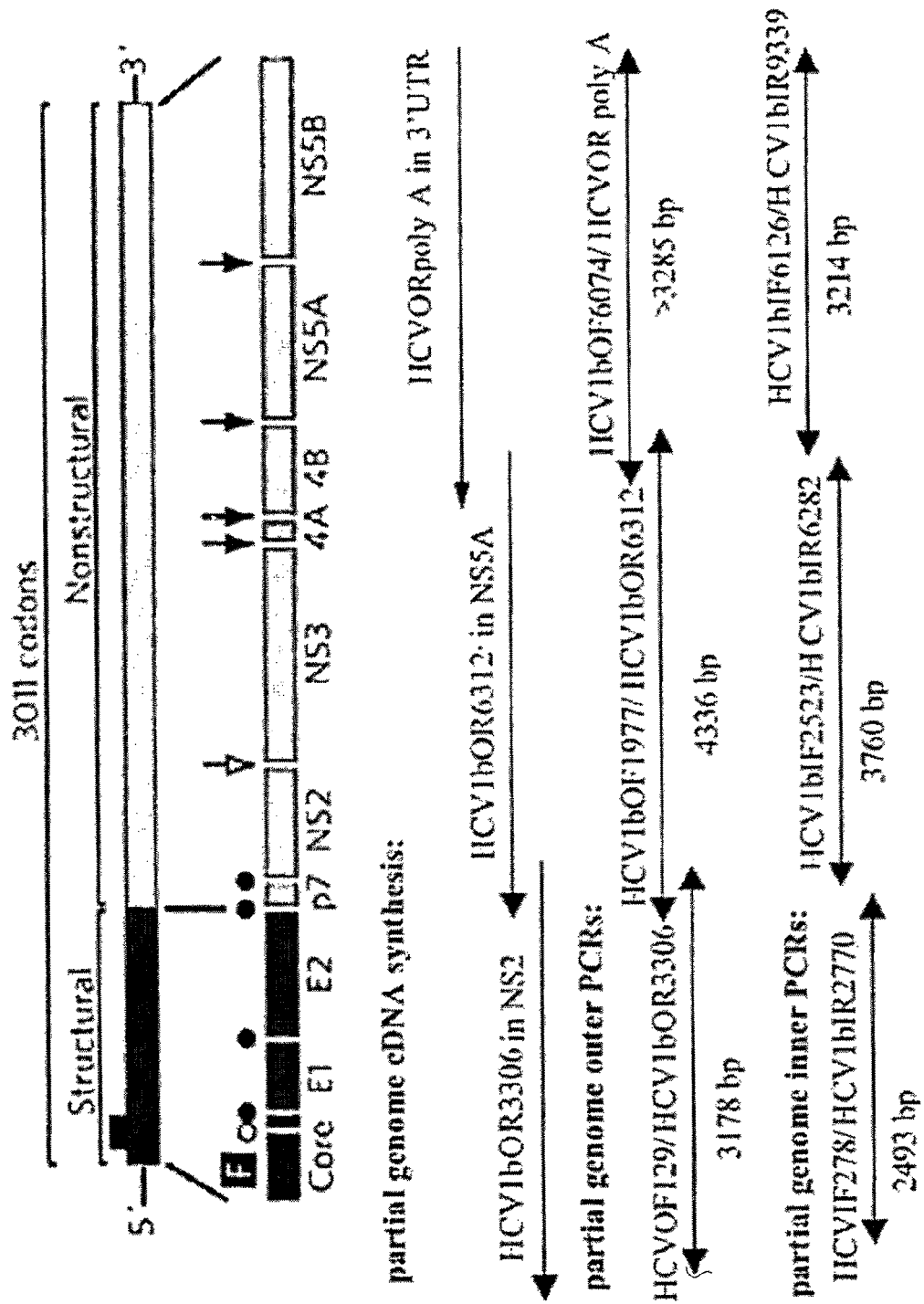
FIG. 1 schematically represents the partial cDNA synthesis and amplification steps of assays of the invention on the example of an HCV type 1b.

To aid in understanding the invention, several terms are defined below.

The terms "nucleic acid" and "oligonucleotide" refer to primers and oligomer fragments to be amplified or detected, and shall be generic to polydeoxyribonucleotides (containing 2-deoxy-D-ribose), also named DNA, to polyribonucleotides (containing D-ribose), also named RNA, and to any other type of polynucleotide which is an N glycoside of a purine or pyrimidine base, or modified purine or pyrimidine base. There is no intended distinction in length between the terms "nucleic acid" and "oligonucleotide", and these terms will be used interchangeably. These terms refer only to the primary structure of the molecule. Thus, these terms include double- and single-stranded DNA, as well as double- and single-stranded RNA.

The term "cDNA" refers to complementary DNA which is DNA synthesized from an RNA template by the action of RNA-dependent DNA polymerase or reverse transcriptase or DNA polymerase. These terms include double- and single-stranded complementary DNA.

Oligonucleotides can be prepared by any suitable method, including, for example, cloning and restriction of appropriate sequences and direct chemical synthesis by a method such as the phosphotriester method of Narang et al. (1979) Meth Enzymol 68, 90-99; the phosphodiester method of Brown et al. (1979) Meth Enzymol 68, 109-151; the diethylphosphoramidite method of Beaucage et al. (1981) Tetrahedron Lett 22, 1859-1862; and the solid support method of U.S. Pat. No. 4,458,066.

The terms "hybridization" and "hybridize" refer to the formation of a duplex structure by two single-stranded nucleic acids due to complementary base pairing. Hybridization can occur between fully (exactly) complementary nucleic acid strands or between "substantially complementary" nucleic acid strands that contain minor regions of mismatch. Conditions under which only fully complementary nucleic acid strands will hybridize are referred to as "stringent hybridization conditions". Stable duplexes of substantially complementary sequences can be achieved under less stringent hybridization conditions. Those skilled in the art of nucleic acid technology can determine duplex stability empirically following the guidance provided by the art (see, e.g., Sambrook et al. (1985) Molecular Cloning—A Laboratory Manual, Cold Spring Harbor Laboratory, Cold Spring Harbor, N.Y.). Generally, stringent conditions are selected to be about 5° C. lower than the thermal melting point (Tm) for the specific sequence at a defined ionic strength and pH. The Tm is the temperature (under defined ionic strength and pH) at which 50% of the base pairs have dissociated. Relaxing the stringency of the hybridization conditions will allow sequence mismatches to be tolerated; the degree of mismatch tolerated can be controlled by suitable adjustment of the hybridization conditions. Hybridization of both exactly complementary and substantially complementary nucleic acid strands is referred to herein as "specific".

The term "primer" refers to an oligonucleotide capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligodeoxyribonucleotide. The appropriate length of a primer depends on the intended use of the primer but typically ranges from about 15 to about 35 nucleotides. Short primer molecules generally require cooler temperatures to form sufficiently stable hybrid complexes with the template. A primer need not reflect the exact sequence of the template nucleic acid, but must be sufficiently complementary to hybridize with the template. Primers can incorporate additional features which allow for the detection or immobilization of the primer but do not alter the basic property of the primer, that of acting as a point of initiation of DNA synthesis. The region of the primer which is sufficiently complementary to the template to hybridize is referred to herein as the hybridizing region.

As used herein, a "sense" or "upstream" primer refers to a primer whose extension product is a subsequence of the coding strand; an "antisense" or "downstream" primer refers to a primer whose extension product is a subsequence of the complementary non-coding strand.

The terms "outer primer" or "outer primers" refer to the first primer or pair of primers that are used to reverse-transcribe or initially amplify a stretch of a nucleic acid. The terms "inner primer" or "inner primers" refer to a primer or to a pair of primers that are used to further amplify the initial amplification product. Inner primers do not share significant sequence homology with corresponding outer primers, and amplification by inner primers typically produces a secondary amplification product that is slightly shorter than the initial amplification product.

As used herein, an oligonucleotide primer is "specific" for a target sequence if the number of mismatches present between the oligonucleotide and the target sequence is less than the number of mismatches present between the oligonucleotide and non-target sequences. Hybridization conditions can be chosen under which stable duplexes are formed only if the number of mismatches present is no more than the number of mismatches present between the oligonucleotide and the target sequence. Under such conditions, the target-specific oligonucleotide can form a stable duplex only with a target sequence. The use of target-specific primers under suitably stringent amplification conditions enables the specific amplification of those target sequences that contain the target primer binding sites.

The terms "target region" and "target nucleic acid" refers to a region of a nucleic acid that is to be amplified or otherwise analyzed. The sequence to which a primer hybridizes can be referred to as a "target".

The terms "variant" or "HCV variant" refers to an HCV having a genome that differs from that of the corresponding prototype virus by the presence of at least one mutation that causes at least a one amino acid change in a viral protein product. Accordingly, the term "mutation" refers to such changes in the genome of a variant that result in a viral protein product that differs from that of the prototype virus by at least one amino acid.

The term "prototype virus" or "prototype HCV" means a reference HCV virus that provides a reference genome with which the viral sequences produced in the assays of the invention are compared and which serve as a basis for designing the cDNA synthesis, amplification and sequencing primers used in the assays. Prototype virus may refer to a specific virus isolate. Alternatively, it may refer to a hypothetical HCV virus that contains a consensus genome derived from comparison of genomic sequences of multiple virus isolates. One such prototype virus, HCV strain H77 (Genbank Accession Number AF011751), was used in example 1 for designing HCV1b primers. HCV con1 (Genbank Accession Number AJ238799) was used as prototype HCV1b genomic sequence in the assays of example 3. A person skilled in the art will know how to select prototype HCV sequences for other genotypes and subtypes. For example, HCV strains HC-J6 (Genbank Accession Number D00944) or JFH1 (Genbank Accession Number AB047639) may be considered as prototype HCV2a.

The term "quasispecies" relates to a group of highly related HCV of identical genotype and subtype frequently present in an infected subject.

The terms "anti-HCV drug or drug combination" refer to any drug or drug combination, respectively, that is capable of decreasing HCV viral load or viral titer in at least a subset of HCV-infected subjects. In particular, these terms also refer to any drug or drug combination, respectively, that is capable of substantially or significantly decreasing HCV viral load or viral titer in at least a subset of HCV-infected subjects. Anti-HCV drugs include but are not limited to HCV replication inhibitors such as polymerase inhibitors, protease inhibitors and cyclophilin inhibitors, immune or host response modulators, virus entry inhibitors and host factor inhibitors.

The term "data bank of HCV mutations associated with anti-HCV drug resistance" refers to a compilation, in any form, of mutations that are associated with resistance to any anti-HCV drug or drug combination, resistance being indicated by a failure of a course of treatment with an anti-HCV drug or drug combination to substantially reduce viral load (also referred to as treatment failure). Such a data bank may be assembled using information available in the art or becoming available in the art as well as information obtained from analyses of samples from drug-resistant, infected subjects conducted employing the assays of the present invention.

Presently available assays do not indicate whether a member of a population of HCV variants present in a subject (quasispecies) or even whether a predominant variant will be resistant to a treatment with a particular anti-HCV drug or a combination of anti-HCV drugs. Moreover, these tests do not determine which individual mutations, linked mutations or fingerprint within a viral genome are associated with viral resistance to a particular anti-HCV therapy. Most therapies against HCV are very expensive and lengthy. Treating an HCV-infected subject without knowing whether it is a priori resistant to the particular anti-HCV drug or drug combination utilized may result in adverse effects in the subject due to the consequences of the continued presence of virus at high levels as well as to secondary effects (toxicity) of the anti-HCV treatment.

A diagnostic assay for characterizing mutations in a complete or nearly complete HCV genome of a particular genotype and/or subtype that are associated with resistance to a particular anti-HCV drug or drug combination is a long felt need for the person skilled in the art, i.e. a physician, a clinician or a nurse at a hospital or medical care facility. The present invention provides such an assay. The assay relies on amplification by reverse transcription—polymerase chain reaction (RT-PCR) of an HCV genome as three overlapping DNA fragments of similar lengths. The inventors found that amplification of the genome as three fragments represents a best compromise between the need for sensitivity of the assay and avoidance of selection of viral variant sequences. Within limits, sensitivity of the assay would increase with the number of discrete fragments amplified, whereas minimization of selection would require a decrease in the number of discrete fragments amplified. The assays of the invention are highly sensitive and, in contrast to assays based on reverse transcription and amplification of full-length viral genomes, permit detection and analysis of HCV genomes from samples taken from subjects with very low viral loads.

The assays of the invention will enable the systematic assembly of a data bank of mutations that are associated with resistance to particular anti-HCV drugs and, once a useful data set has been assembled, can be employed as prognostic assays for determining the presence in an infected subject of an HCV variant that is resistant to treatment with a particular anti-HCV drug(s). Based on such information, it will be possible to select an appropriate anti-HCV drug or drug combination for a therapy of the infected subject that will not be hampered by drug resistance of a detectable HCV variant already present in the subject prior to therapy. Moreover, once a particular therapeutic regimen is selected and treatment of the subject has been initiated, virus isolated from the subject could be introduced into an infectious cell culture model and allowed to undergo a few rounds of replication under the selective pressure of the drug or drug combination used on the subject. An assay of the invention could then be performed on the selected virus population to determine whether amplification had occurred of a minor drug-resistant variant that could not be detected prior to such amplification. Results obtained could be utilized to rapidly adapt or change the drug regimen administered to the subject.

In addition to measurements of viral load, an assay of the invention could be employed for monitoring development of drug resistance in a subject treated with an anti-HCV drug or drug combination. Virus would be isolated at the end of a course of therapy or at various times during treatment and analysed using an assay of the invention. Detection of a major variant containing a known resistance mutation or set of linked mutations would provide an indication, which is independent from determinations of viral load, that the therapeutic regimen needs be adapted or replaced by another regimen. The above-mentioned data bank of mutations would assist the treating physician in the choice of an adapted or alternative regimen.

The assays of the present invention are highly sensitive and enable detection, by a single procedure, of individual mutations or linked mutations occurring essentially anywhere in an HCV genome that are associated with resistance to a treatment with any combination of one or more anti-HCV drugs.

The practice of the present invention will employ, unless otherwise indicated, conventional techniques of molecular biology, microbiology, recombinant DNA, polypeptide and nucleic acid synthesis, and immunology, which are within the skill of the art. Such techniques are explained fully in the literature. See e.g., Sambrook et al., (1989) Molecular Cloning—A Laboratory Manual, Cold Spring Harbor Laboratory, Cold Spring Harbor, N.Y.; DNA Cloning—a Practical Approach, volumes 1 and 2 (D. M. Glover, ed., 1985); Oligonucleotide Synthesis (M. J. Gait, ed., 1984); Nucleic Acid Hybridization (B. D. Hames & S. J. Higgins, eds., 1984); Transcription and Translation (B. D. Hames & S. J. Higgins, eds., 1984); Animal Cell Culture—a Practical Approach (R. I. Freshney, ed., 1986); Immobilized Cells and Enzymes—A Practical Approach (J. Woodward, ed., 1985); B. Perbal (1984) A Practical Guide to Molecular Cloning, John Wiley & Sons, New York, N.Y.; the series Methods in Enzymology, Academic Press, Inc., including volume 154 (R. Wu & L. Grossman, eds., 1987) and volume 155 (R. Wu, ed., 1987); Gene Transfer Vectors for Mammalian Cells (J. H. Miller & M. P. Calos, eds., 1987); Immunochemical Methods in Cell and Molecular Biology (R. J. Mayer & J. H. Walker, eds., 1987), Protein Purification—Principles and Practice (R. K. Scopes, 1987); and Handbook of Experimental immunology, volumes 1-4 (D. M. Weir & C. C. Blackwell, eds., 1986).

In the most general embodiment, the present invention relates to an assay that is capable of identifying and characterizing single and linked mutations in a genome of an HCV variant present in a sample, the assay comprising the following steps that are carried out sequentially:

Step 1: extraction of viral RNA from a sample containing an HCV;

Step 2: determination of genotype and subtype of the HCV;

Step 3: synthesis of partial cDNAs of the genome of the HCV in three separate reverse transcription reactions, the first reverse transcription reaction initiated from a first outer antisense primer selected to specifically hybridize to a sequence in the 3'UTR of a prototype HCV of the same genotype and subtype, the second reverse transcription reaction initiated from a second outer antisense primer selected to specifically hybridize to a sequence in the NS4B-NS5A region of the genome of the prototype HCV and the third reverse transcription reaction initiated from a third outer antisense primer selected to specifically hybridize to a sequence in the NS2 region of the genome of the prototype HCV;

Step 4: second strand synthesis and amplification of the partial cDNAs of the genome of the HCV in three separate PCR reactions, the first PCR reaction comprising an aliquot of the first reverse transcription reaction, the first outer antisense primer and a first outer sense primer selected to specifically hybridize to a complement of a sequence in the NS4B-NS5A region of the genome of the prototype HCV, the second PCR reaction comprising an aliquot of the second reverse transcription reaction, the second outer antisense primer and a second outer sense primer selected to specifically hybridize to a complement of a sequence in the NS2 region of the genome of the prototype HCV, and the third PCR reaction comprising an aliquot of the third reverse transcription reaction, the third outer antisense primer and a third outer sense primer selected to specifically hybridize to a complement of a sequence in the 5'UTR region of the genome of the prototype HCV, wherein the second outer antisense primer hybridizes to a sequence in the NS4B-NS5A region of the genome of the prototype HCV that is located 3' to the region that is complementary to the first outer sense primer and wherein the third outer antisense primer hybridizes to a sequence in the NS2 region of the genome of the prototype HCV that is located 3' to the region that is complementary to the second outer sense primer;

Step 5: further amplification of the partial cDNAs of step 4 in three separate nested PCR reactions, the first nested PCR reaction comprising an aliquot of the first PCR reaction and first inner antisense and sense primers, the second nested PCR reaction comprising an aliquot of the second PCR reaction and second inner antisense and sense primers, and the third nested PCR reaction comprising an aliquot of the third PCR reaction and third inner antisense and sense primers, wherein the inner primers do not overlap the outer primers, the second inner antisense primer hybridizes to a sequence in the NS4B-NS5A region of the genome of the prototype HCV that is located 3' to the region that is complementary to the first inner sense primer and the third inner antisense primer hybridizes to a sequence in the NS2 region of the genome of the prototype HCV that is located 3' to the region that is complementary to the second inner sense primer;

Step 6: sequence analysis of the further amplified cDNAs of step 5; and

Step 7: comparison of the sequences obtained with that of the prototype HCV.

In a more specific embodiment, the present invention relates to an assay that is capable of identifying and characterizing single and linked mutations in a genome of an HCV variant resistant to an anti-HCV drug or drug combination in a sample taken from a subject that has been undergoing treatment with the anti-HCV drug or drug combination. The assay comprises the following steps that are carried out sequentially:

Step 1: extraction of viral RNA from a sample taken from a subject harboring an HCV that is resistant to an anti-HCV drug or drug combination with which the subject has been treated;

Steps 2-6 as in the assay described above;

Step 7: comparison of the sequences obtained in step 6 with that of the genome of the prototype HCV and identification of mutations; and Step 8: entry of the mutations identified in a data bank of mutations associated with anti-HCV drug resistance.

Once a useful data bank of mutations associated with drug resistance has been established, the present invention will also relate to an assay that is identical to the assay described immediately before, except that step 8 will consist of a search of the data bank for the mutations identified and selection of an alternative anti-HCV drug or drug combination to which the HCV is not expected to be resistant for subsequent treatment of the subject.

The latter assay of the invention may also be carried out on a sample taken from a subject infected with HCV prior to commencement of any pharmacological therapy of the subject. Results from the assay will allow the physician to select an anti-HCV drug or drug combination to which the HCV the subject is infected with is not resistant. It is realized that a subject frequently is infected with a quasispecies of HCV comprising a dominant variant and multiple, minor variants. The assay primarily will uncover mutations present in the dominant variant. Whether mutations present in minor variants will also be discoverable will depend on multiple factors, in particular on the relative abundance of minor variants and the sequencing technology employed. Mutations in a minor variant should be identifiable by routine capillary sequencing, i.e., standard automated sequencing, if the relative abundance of the minor variant is at least about 20%. If representation of a variant is lower, an advanced sequencing methodology such as high-throughput sequencing-by-synthesis technologies will need to be utilized to obtain mutational information. Such sequencing technologies were developed, e.g., by Illumina Inc., San Diego, Calif., 454 Life Sciences, Branford, Conn., and Applied Biosciences, Foster City, Calif. Sequencing equipment and services are commercially available.

Specific embodiments of assays for use with samples containing an HCV1b variant are presented below and are further illustrated in the Example section. One such assay comprises the following steps that are carried out in sequence:

Step 1: extraction of viral RNA from a sample containing an HCV;

Step 2: determination of genotype and subtype of the HCV;

Step 3: provided that step 2 indicated that the HCV is of type 1b, synthesis of partial cDNAs of the genome of the HCV in three separate reverse transcription reactions, the first reverse transcription reaction initiated from primer poly-A, the second reverse transcription reaction initiated from primer HCV1bOR6312 and the third reverse transcription reaction initiated from primer HCV1bOR3306;

Step 4: second strand synthesis and amplification of the partial cDNAs of the genome of the HCV in three separate PCR reactions, the first PCR reaction comprising an aliquot of the first reverse transcription reaction and primer pair poly-A/HCV1bOF6074, the second PCR reaction comprising an aliquot of the second reverse transcription reaction and primer pair HCV1bOR6312/HCV1bOF1977 and the third PCR reaction comprising an aliquot of the third reverse transcription reaction and primer pair HCV1bOR3306/HCVOF129;

Step 5: further amplification of the partial cDNAs of step 4 in three separate nested PCR reactions, the first nested PCR reaction comprising an aliquot of the first PCR reaction and primer pair HCV1bIR9339/HCV1bIF6126, the second nested PCR reaction comprising an aliquot of the second PCR reaction and primer pair HCV1bIR6282/HCV1bIF2523, and the third nested PCR reaction comprising an aliquot of the third PCR reaction and primer pair HCV1bIR2770/HCVIF278;

Step 6: sequence analysis of the further amplified cDNAs of step 5; and

Step 7: comparison of the sequences obtained with that of a prototype HCV1b.

Another such assay for use with samples obtained from a subject harboring an HCV1b that is resistant to the therapy the subject has received comprises the following steps that are carried out in sequence:

Step 1: extraction of viral RNA from a sample taken from a subject infected with an HCV that is resistant to an anti-HCV drug or drug combination with which the subject has been treated;

Steps 2-6 as in the preceding assay;

Step 7: comparison of the sequences obtained in step 6 with that of the genome of the prototype HCV and identification of mutations; and Step 8: entry of the mutations identified in a data bank of mutations associated with anti-HCV drug resistance.

A similar assay that can be carried out once a useful data bank of HCV1b mutations associated with drug resistance has been generated is identical to the assay described immediately before, except that step 8 will consist of a search of the latter data bank for the mutations identified and selection of an alternative anti-HCV drug or drug combination to which the HCV is not expected to be resistant for subsequent treatment of the subject.

The above assay may also be carried may also be carried out on a sample taken from a subject infected with HCV prior to commencement of any pharmacological therapy of the subject. Provided that the HCV of the subject is of type 1b, results from the assay would allow the physician to select an anti-HCV drug or drug combination to which the HCV the subject is infected with is not resistant.

Key aspects of the above HCV1b-specific assays are also illustrated in FIG. 1 and in the Example section. The nucleotide sequences of cDNA synthesis and amplification primers as well as a set of proposed sequencing primers are provided in Table 1.

TABLE 1

HCV 1b primers

| Primer name | Purpose | Direction | Primer sequence | Location in the genome (H77 as reference) | SEQ ID NO: |
|---|---|---|---|---|---|
| HCV1bOR3306 | cDNA/outer PCR 5'UTR-NS2 region | antisense | GATGATGTCCCCAC ACGCCGCGGTGTC | 3332-3306 | 3 |
| HCVOF129 | outer PCR 5'UTR-NS2 region | sense | CCGGGAGAGCCATAG TGGTCTGCGGAACC | 129-157 | 6 |
| HCVIF278 | inner PCR 5'UTR-NS2 region | sense | GCCTTGTGGTACTGC CTGATAGGGTGCTTG | 278-307 | 12 |
| HCV1bIR2770 | inner PCR 5'UTR-NS2 region | antisense | TCCGCACGATGCAGC CATCTCCCGGTCCA | 2798-2770 | 9 |
| HCV1bOR6312 | cDNA/outer PCR NS2-NS5A region | antisense | GGCAGGAGCTTGGAC TGGAGCCAGGTCTTG AA | 6343-6312 | 2 |
| HCV1bOF1977 | outer PCR NS2-NS5A region | sense | CAAGGCAACTGGTTC GGCTGTACATGGATG AA | 1977-2008 | 5 |
| HCV1bIF2523 | inner PCR NS2-NS5A region | sense | GACGCGCGCGTCTGY GCCTGCTTRTGGAT | 2523-2551 | 11 |
| HCV1bIR6282 | inner PCR NS2-NS5A region | antisense | TCAGTCAACACCGTG CATATCCAGTCCCA | 6310-6282 | 8 |
| poly-A | cDNA/outer PCR NS4B-3'UTR region | antisense | 30-mer | 9447-9418 | 1 |
| HCVOF6074 | outer PCR NS4B-3'UTR region | sense | GGCTGTGCAGTGGAT GAACCGGCTGATAGC | 6074-6103 | 4 |
| HCV1bIF6126 | inner PCR NS4B-3'UTR region | sense | GTCTCCCCCACGCA CTATGTGCCTGA | 6126-6151 | 10 |
| HCV1bIR9339 | inner PCR NS4B-3'UTR region | antisense | GGGAGCAGGTAGA TGCCTACCCCTAC | 9367-9342 | 7 |

TABLE 1-continued

HCV 1b primers

| Primer name | Purpose | Direction | Primer sequence | Location in the genome (H77 as reference) | SEQ ID NO: |
|---|---|---|---|---|---|
| HCV1bSF310 | sequencing 5'UTR-NS2 region | sense | GAGTGCCCCGGGAGGTCTTCGTAGA | 309-332 | 13 |
| HCV1bSF807 | sequencing 5'UTR-NS2 region | sense | CCGGGTTCTGGAGGACGGCGTGAA | 806-829 | 14 |
| HCV1bSR850 | sequencing 5'UTR-NS2 region | antisense | AGGAAGATAGAGAAAGAGCAACCGGG | 874-849 | 15 |
| HCV1bSF1202 | sequencing 5'UTR-NS2 region | sense | TCTCCCAGCTGTTCACCTTCTC | 1201-1222 | 16 |
| HCV1bSR1302 | sequencing 5'UTR-NS2 region | antisense | GACCAGTTCATCATCATATCC | 1321-1301 | 17 |
| HCV1bSF1597 | sequencing 5'UTR-NS2 region | sense | GGCAGCTGGCACATCAACAGGAC | 1593-1615 | 18 |
| HCV1bSR1653 | sequencing 5'UTR-NS2 region | antisense | GTAGAACAGCGCGGCAAGGAAC | 1674-1653 | 19 |
| HCV1bSF1854 | sequencing 5'UTR-NS2 region | sense | TGGTCCAGTGTATTGYTTCACCC | 1850-1872 | 20 |
| HCV1bSR1990 | sequencing 5'UTR-NS2 region | antisense | TTCATCCATGTACAGCCGAACCA | 2008-1986 | 21 |
| HCV1bSF2242 | sequencing 5'UTR-NS2 region | sense | GTGGGGGGCGTGGAGCACAGGC | 2238-2259 | 22 |
| HCV1bSR2433 | sequencing 5'UTR-NS2 region | antisense | CGTACAGGTATTGCACGTCCACG | 2451-2429 | 23 |
| HCV1bSF2640 | sequencing NS2-NS5A region | sense | TCTCTCCTTCCTTGTGTTCTTCT | 2636-2658 | 24 |
| HCV1bSF2860 | sequencing NS2-NS5A region | antisense | AACCACCATATGAGCCTGGCGAG | 2882-2860 | 25 |
| HCV1bSF3085 | sequencing NS2-NS5A region | sense | CGCGCTCAAGGGCTCATYCGTG | 3081-3102 | 26 |
| HCV1bSR3280 | sequencing NS2-NS5A region | antisense | CAGGTGATGATCTTGGTCTCCAT | 3298-3276 | 27 |
| HCV1bSF3541 | sequencing NS2-NS5A region | sense | ACRCAATCTTTCCTGGCGACCTG | 3537-3559 | 28 |
| HCV1bSR3643 | sequencing NS2-NS5A region | antisense | GTCCTGGTCTACATTGGTGTACAT | 3662-3639 | 29 |
| HCV1bSF4004 | sequencing NS2-NS5A region | sense | CGCAGACATTCCAAGTGGCCCA | 4000-4021 | 30 |
| HCV1bSR4237 | sequencing NS2-NS5A region | antisense | CAACCACCGTCGGCAAGGAACTT | 4255-4233 | 31 |
| HCV1bSF4516 | sequencing NS2-NS5A region | sense | CTCATTTTCTGCCATTCAAGAA | 4512-4534 | 32 |
| HCV1bSR4666 | sequencing NS2-NS5A region | antisense | TCAAAGTCGCCGGTAWAGCCCGTCAT | 4687-4662 | 33 |
| HCV1bSF5048 | sequencing NS2-NS5A region | sense | TAGATGCCCACTTCTTGTCCC | 5044-5064 | 34 |
| HCV1bSR5164 | sequencing NS2-NS5A region | antisense | AGCCGTATGAGACACTTCCACAT | 5182-5160 | 35 |
| HCV1bSF5524 | sequencing NS2-NS5A region | sense | CAATTCAAGCAGAAGGCGCTCGG | 5520-5542 | 36 |

TABLE 1-continued

HCV 1b primers

| Primer name | Purpose | Direction | Primer sequence | Location in the genome (H77 as reference) | SEQ ID NO: |
|---|---|---|---|---|---|
| HCV1bSR5639 | sequencing NS2-NS5A region | antisense | TGTATCCCGCTGAT GAARTTCCACA | 5659-5635 | 37 |
| HCV1bSF5986 | sequencing NS2-NS5A region | sense | ACACGCTGTGATAA ATGTCTCCCCGC | 5986-6008 | 38 |
| HCV1bSR6092 | sequencing NS2-NS5A region | antisense | GAAGCGAACGCTAT CAGCCGGTTCA | 6112-6088 | 39 |
| HCV1bSF6186 | sequencing NS2-NS5A region | sense | CCTCTCCAGCCTTA CCATCACTCA | 6182-6205 | 40 |
| HCV1bSR6256 | sequencing NS2-NS5A region | antisense | TCCCTIAGCCACGA GCCGGAGCATGG | 6281-6256 | 41 |
| HCV1bSF6416 | sequencing NS4B-3'UTR region | sense | TCATGCAIACCACCT GCCCATG | 6416-6437 | 42 |
| HCV1bSR6616 | sequencing NS4B-3'UTR region | antisense | TCCCCCACCCGCG TGACCTCCAC | 6639-6616 | 43 |
| HCV1bSF6853 | sequencing NS4B-3'UTR region | sense | GTGCTCACTTCCAT GCTCACCGA | 6849-6871 | 44 |
| HCV1bSR6964 | sequencing NS4B-3'UTR region | antisense | TCAAGGAAGGCGC AGACAACTG | 6975-6954 | 45 |
| HCV1bSF7066 | sequencing NS4B-3'UTR region | sense | GGGAACATCACCC GCGTGGAGTC | 7056-7078 | 46 |
| HCV1bSR7273 | sequencing NS4B-3'UTR region | antisense | GGGCACCCGTGTA CCACCGGAGG | 7285-7263 | 47 |
| HCV1bSF7504 | sequencing NS4B-3'UTR region | sense | TACTCCTCCATGCC CCCCCTTGA | 7494-7516 | 48 |
| HCV1bSR7558 | sequencing NS4B-3'UTR region | antisense | CTCGCTCACRGTAG ACCAAGACCC | 7570-7548 | 49 |
| HCV1bSF7968 | sequencing NS4B-3'UTR region | sense | CTCCGTGTGGAAG GACTTGCTGGA | 7961-7984 | 50 |
| HCV1bSR8077 | sequencing NS4B-3'UTR region | antisense | TCTGGGAATACGAT AAGGCGAGC | 8092-8070 | 51 |
| HCV1bSF8528 | sequencing NS4B-3'UTR region | sense | AGCTCCAGGACTG CACGATGCT | 8521-8542 | 52 |
| HCV1bSR8622 | sequencing NS4B-3'UTR region | antisense | TACCTAGTCATAGC CTCCGTGAAG | 8638-8615 | 53 |
| HCV1bSF9010 | sequencing NS4B-3'UTR region | sense | ACACGCTGTGATAA ATGTCTCCCCGC | 9010-9032 | 54 |
| HCV1bSR9094 | sequencing NS4B-3'UTR region | antisense | GATGTCTCCAGACT CGCAAGGG | 9108-9087 | 55 |

Other specific embodiments of the invention relate to analogous assays for use with samples obtained from subjects infected with HCV of other genotypes and subtypes, in particular HCV1a, HCV2 and HCV3. A person skilled in the art will know how to design appropriate cDNA synthesis and amplification primers according to the method of the invention as well as sequencing primers by reference to prototype viral genome sequences.

Samples may consist of but are not limited to blood samples of subjects infected by HCV or co-infected by HIV and HCV, which samples may be taken from the subjects prior to, during or subsequent to a course of treatment with an anti-HCV drug or drug combination. The assays of the invention may be used for other applications. For example, HCV variants present in a sample from a subject may be cloned into an infectious HCV vector and transduced into mammalian cells. (Kato et as. (2007) J Virol 81, 4405-4411). Infectious virus containing HCV variant sequences may thereafter be used to infect mammalian cultures, and samples obtained after one or several cycles of infection in the presence or absence presence of an anti-HCV drug or drug combination may be analysed by the assays of the invention.

HCV RNA extraction from samples may be performed by various methods including the use of commercially available kits, e.g., QIAamp® Viral RNA mini kit, QIAamp® Utralsens™ Virus Kit, Trizol reagens (Invitrogen) or Vivaspin concentration.

The reverse transcription and PCR reactions that are part of the assays are performed using standard reaction mixtures and conditions such as those described in the examples and the references cited herein. Typically, nucleic acids extracted from samples are subjected to 20-40 amplification cycles in the PCR reactions of steps 4 and 2-10 cycles in the nested PCR reaction of steps 5.

All publications and patents cited herein shall be considered as incorporated by reference in their entirety.

The invention is further elaborated by the following examples. The examples are provided for purpose of illustration to a person skilled in the art, and are not intended to be limiting the scope of the invention as described in the claims. Thus, the invention should not be construed as being limited to the examples provided, but should be construed to encompass any and all variations that become evident as a result of the teaching provided herein.

EXAMPLES

Example 1

Detailed Methods used in the Assays of the Invention

Samples: Plasma samples from therapy-naive patients were obtained from two different hospitals. Viral load was determined using the HCV Viral Load COBAS AMPLICOR system from Roche Molecular Diagnostics (Basel, Switzerland).

Samples were selected based on the presence of HCV of type 1b as determined by InnoLipa test (Innogenetics, Zwijnaarde, Belgium). To confirm genotype, after cDNA synthesis and PCR amplification with one set of outer primer pairs, sequencing was performed with one of the latter primers. The resulting sequence was genotyped and subtyped using the Oxford Automated HCV Subtyping tool. (De Oliveira et al. (2005) Bioinformatics 21, 3797-3800.)

Primer selection and synthesis: Primers for reverse transcription, PCR amplification and sequencing were developed using the OLIGO software (Medprobe, Oslo, Norway). Aligned near-full length genome sequences were downloaded from the Los Alamos HCV database (http://hcv.lanl.gov/content/sequence/HCV/ToolsOutline.html). The primer sequences for HCV1b are given in Table 1. The primers were synthesised by Applera Europe (Lennik, Belgium).

RNA extraction: RNA extraction was performed using the QIAamp Viral RNA mini kit from Qiagen (Westburg, Leusden, The Netherlands) according to the manufacturer's protocol.

cDNA synthesis and PCR amplification: RNA was reverse-transcribed in three separate reactions (primed by the three outer antisense primers) with Transcriptor RT from Roche (Roche Diagnostics, Mannheim, Germany). First, 2.5 µM outer antisense primer and 10 µl RNA were denatured in a microtube for 5 min at 65° C. and snap-cooled. Next, a reverse transcription mixture was assembled in a final volume of 20 µl, the mixture including the following additional components: 1× Transcriptor RT-buffer, 1 mM dNTP's, 20 U of Protector RNase Inhibitor, 10 U of Transcriptor Reverse Transcriptase and MilliQ water. cDNA synthesis was performed at 50° C. for 90 minutes, and reactions were then cooled down to 4° C. PCR amplification was done in two steps using the Expand Long Template PCR System from Roche (Roche Diagnostics, Mannheim, Germany). A first set of PCR was performed under the following conditions: 1× Expand Long Template Buffer 1, 0.350 mM dNTP's, 0.3 µM outer sense primer, 0.3 µM outer antisense primer, 3.75 U Expand Long Template DNA Polymerase, 5 µl template cDNA and MilliQ water in a final volume of 50 µl. Subsequent to a denaturation step at 94° C. for 2 min, 10 cycles of 10 sec at 94° C., 30 sec at 57° C., and 4 min at 68° C. were performed. This amplification was followed by 25 cycles of 15 sec at 94° C., 30 sec at 57° C., and 4 min at 68° C., with a time increment of 20 sec/cycle and a final elongation step of 7 min at 68° C. The reactions were then cooled to 4° C. A second set of PCR was performed under the following conditions: 1× Expand Long Template Buffer 1, 0.350 mM dNTP's, 0.3 µM inner sense primer, 0.3 µM inner antisense primer, 3.75 U Expand Long Template DNA Polymerase, 2 µl amplification product from the first set of PCR and MilliQ water in a final volume of 50 µl. Cycling conditions were identical to those of the first set of PCR except that only three cycles were performed.

Gel electrophoresis: PCR products were analyzed by agarose gel electrophoresis. 7.5 µl of PCR product were loaded on a 1.5% agarose gel, and electrophoresis was performed at 100V. Gels were stained for 10 min with ethidium bromide for visualising DNA fragments.

PCR product purification: PCR products were purified using the Qiaquick PCR purification kit from Qiagen (Westburg, Leiden, The Netherlands) according to the manufacturer's protocol. Concentration of purified PCR products was determined spectrophotometrically. Sequencing reactions required about 2 ng/100 by of DNA.

Nucleotide sequencing: Sequencing reactions were performed at Fasteris SA (Geneva, Switzerland) using the BigDye Terminator v3.1 Cycle Sequencing kit (Applied Biosystems Inc., Foster City, USA). Contigs were assembled and the data were analysed in Seqscape (Applied Biosystems Inc., Foster City, USA).

Example 2

Validation of Assays of the Invention: PCR Success Rate, and Reproducibility and Sensitivity of an Assay of the Invention The rate of success in obtaining visualizable and sequencable quantities of three overlapping PCR products representing nearly the entire viral genome from HCV1b-containing samples was determined using 60 samples from infected subjects that were originally genotyped as HCV1b by Inno-LiPA HCV I. Genotypes/subtypes were re-analyzed by sequencing and phylogenetic analysis for samples with equivocal results.

Reproducibility of the assay was assessed for each partial genome PCR by triplicate testing of samples of confirmed genotype 1b. At least 2 of the 3 repeat testings were performed starting from plasma sample. Exceptionally, the 3rd repeat testing was started from the extracted RNA for samples with insufficient plasma volumes.

Sensitivity of the assay was validated on 10 samples.

Figure 2:
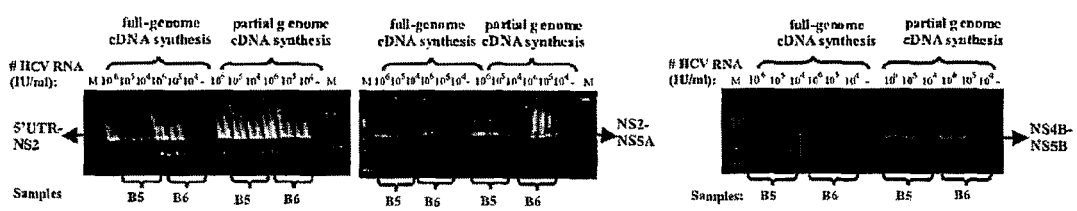
FIG. 2 compares the sensitivity of the partial cDNA amplification method of the invention with that of amplification of full-length viral genomes.

Specificity of the assay was estimated by partial sequencing of PCR products produced from a subset of 8 samples. All sequences were either HCV1b or 1a. Results of these analyses are summarized in Table 2 below. Example results of the sensitivity determinations are presented in FIG. 2.

The data presented in Table 2 demonstrate that PCR success rate approached 100% after subtype correction. The assay was HCV genotype 1-specific. Good reproducibility was observed. Sensitivity was excellent for the 5'UTR-NS2 and NS2-NS5A regions, and acceptable for the NS4B-NS5B region.

TABLE 2

Table 2: PCR success rate, and reproducibility and sensitivity of an assay of the invention

| Pairs of primers | HCV genome region | PCR success rate InnoLipa-typed as HCV1b | PCR success rate sequence-typed as HCV1b | Reproducibility | Sensitivity (copies/reaction) |
|---|---|---|---|---|---|
| HCV1bOR3306/ HCVOF129 | 5'UTR-NS2 | 46/60 (82%) | 45/47 (96%) | 27/45 (3 of 3 tests) 16/45 (2 of 3 tests) 2/45 (1 of 3 tests) | 1-10 |
| HCV1bOR6312/ HCV1bOF1977 | NS2-NS5A | 55/60 (92%) | 44/47 (94%) | 17/44 (3 of 3 tests) 22/44 (2 of 3 tests) 5/44 (1 of 3 tests) | 10-100 |
| poly-A/ HCV1bOF6074 | NS4B-NS5B | 54/60 (90%) | (45/47) (96%) | 19/45 (3 of 3 tests) 18/45 (2 of 3 tests) 8/45 (1 of 3 tests) | 100-1000 |

Example 3

Figure 3A:
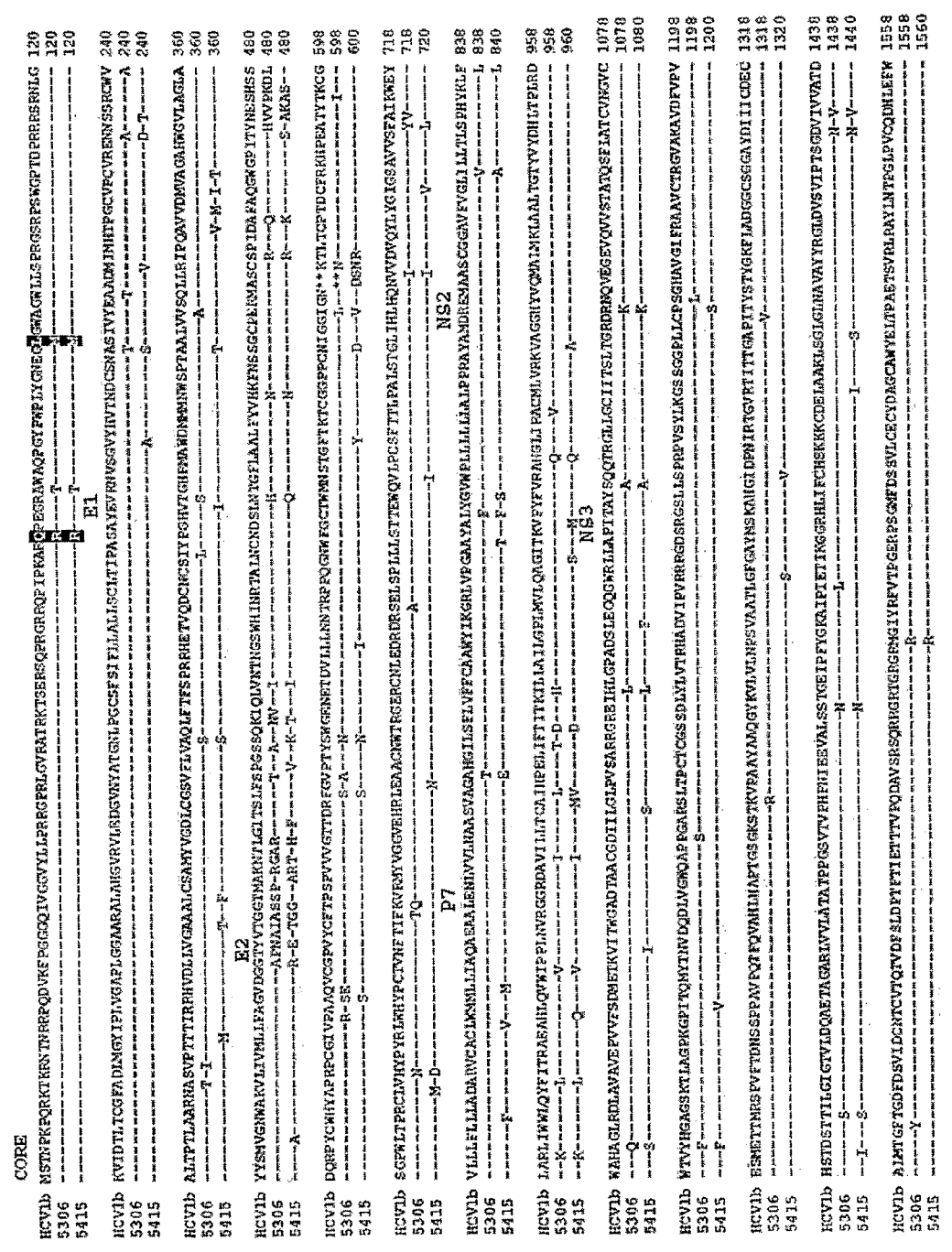
Figure 3B:
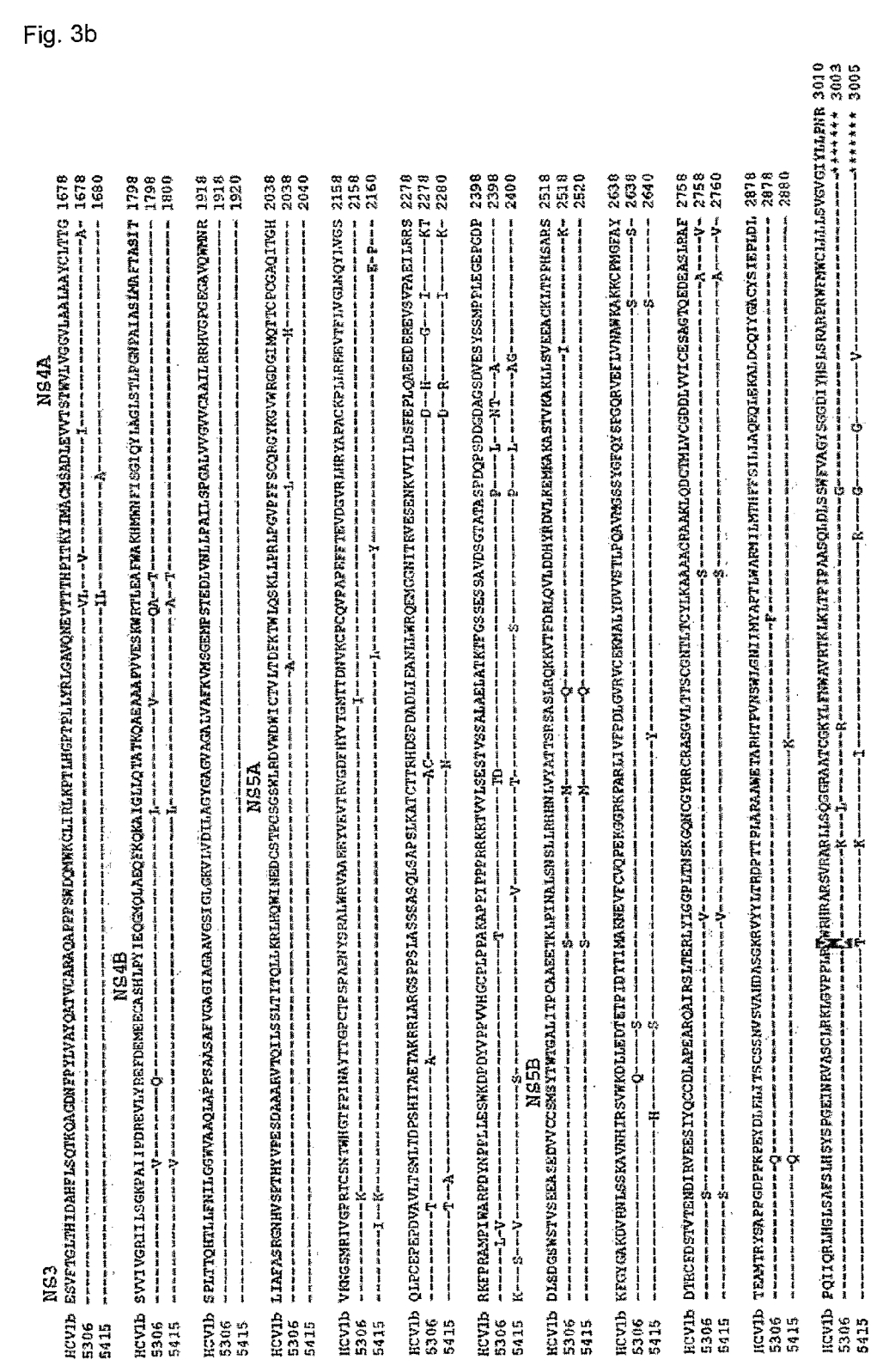

Analysis of Samples from Treatment-Naïve, HCV-Infected Subjects by Means of an Assay of the Invention Aliquots of plasma samples of treatment-naïve, HCV-infected subjects were analysed by an assay of the invention (the assay of claim 5). Nucleic acid sequences obtained after sequencing were automatically translated into amino acids and compared/aligned with clustalw2.0 program (at EBIsite) to an HCV1b consensus sequence, HCV con1 (Genbank Accession Number AF011751). Sequences 5306 and 5415 are from two therapy-naïve, infected subjects. Translated amino acid sequences derived from HCV present in the two subjects are compared to the con1 sequence in FIGS. 3a and 3b. Sequence identity with the consensus sequence is indicated by dash in the sequences from the infected subjects. The beginning of the coding sequence for each viral protein is indicated (CORE, E1, E2, P7, NS2, NS3, NS4A, NS4B, NS5A, NS5B).

The amino acid sequences derived from HCV present in the naïve, infected subjects reveal the presence of mutations L91M in the core protein associated with resistance to IFN/Ribavirin therapy and V499A in NS5B associated with resistance to non-nucleoside inhibitors or benzimidazole compounds. See Table 3 for relevant published information.

TABLE 3

Summary of some amino acid mutations found in the HCV1b genome of subjects or HCV replicons that are associated with drug resistance

| Protein region in HCV1b | Mutations | Drug Resistance | Publication reference |
|---|---|---|---|
| Core | L91M | IFN/Ribavirin therapy | Akuta et al, Virology, 2005 |
| NS5B | V499A | Non-nucleoside inhibitor, benzimidazole compounds | Kukolj et al., JBC, 2005; Hwu et al., Antivir. Res., 2008 |
| NS5A | T245A | IFN/Ribavirin therapy in HCV 1a-infected subjects | Nousbaum et al., J. Virology, 2000 |
| NS3 | C16S/C | ACH806 | Yang et al., Antimicrob. Agent Chem., 2008 |

The invention claimed is:

1. An assay for identifying a mutation in the genome of an HCV present in a sample, the assay comprising the sequential steps of:
   a) extraction of viral RNA from the sample containing the HCV;
   b) determination of genotype and subtype of the HCV;
   c) synthesis of partial cDNAs of the genome of the HCV in three separate reverse transcription reactions, the first reverse transcription reaction initiated from a first outer antisense primer selected to specifically hybridize to a sequence in the 3'UTR of a prototype HCV genome of the same genotype and subtype, the second reverse transcription reaction initiated from a second outer antisense primer selected to specifically hybridize to a sequence in the NS4B-NS5A region of the genome of the prototype HCV and the third reverse transcription reaction initiated from a third outer antisense primer selected to specifically hybridize to a sequence in the NS2 region of the genome of the prototype HCV;
   d) second strand synthesis and amplification of the partial cDNAs of step c) in three separate PCR reactions, the first PCR reaction comprising an aliquot of the first reverse transcription reaction, the first outer antisense primer and a first outer sense primer selected to specifically hybridize to a complementary sequence in the NS4B-NS5A region of the genome of the prototype HCV, the second PCR reaction comprising an aliquot of the second reverse transcription reaction, the second outer antisense primer and a second outer sense primer selected to specifically hybridize to a complementary sequence in the NS2 region of the genome of the prototype HCV, and the third PCR reaction comprising an aliquot of the third reverse transcription reaction, the third outer antisense primer and a third outer sense primer selected to specifically hybridize to a complementary sequence in the 5'UTR region of the genome of the prototype HCV, wherein the second outer antisense primer hybridizes to a sequence in the NS4B-NS5A region of the genome of the prototype HCV that is located 3' to the region that is complementary to the first outer sense primer and wherein the third outer antisense primer hybridizes to a sequence in the NS2 region of the genome of the prototype HCV that is located 3' to the region that is complementary to the second outer sense primer;
   e) further amplification of the partial cDNAs of step d) in three separate nested PCR reactions, the first nested PCR reaction comprising an aliquot of the first PCR reaction and first inner antisense and sense primers, the second nested PCR reaction comprising an aliquot of the second PCR reaction and second inner antisense and sense primers, and the third nested PCR reaction comprising an aliquot of the third PCR reaction and third inner antisense and sense primers, wherein the inner primers do not overlap the outer primers, the second inner antisense primer hybridizes to a sequence in the NS4B-NS5A region of the genome of the prototype HCV that is located 3' to the region that is complementary to the first inner sense primer and the third inner antisense primer hybridizes to a sequence in the NS2 region of the genome of the prototype HCV that is located 3' to the region that is complementary to the second inner sense primer;
   f) sequence analysis of the further amplified cDNAs of step e); and
   g) comparison of the sequences obtained from step f) with that of the prototype HCV.

2. An assay for identifying and characterizing single and linked mutations in a genome of an HCV resistant to an anti-HCV drug, the assay comprising the sequential steps of:
   a) extraction of viral RNA from a sample taken from a subject carrying an HCV that is resistant to an anti-HCV drug or drug combination with which the subject has been treated as indicated by treatment failure;
   b) determination of genotype and subtype of the HCV;
   c) synthesis of partial cDNAs of the genome of the HCV in three separate reverse transcription reactions, the first reverse transcription reaction initiated from a first outer antisense primer selected to specifically hybridize to a sequence in the 3'UTR of a prototype HCV genome of the same genotype and subtype, the second reverse transcription reaction initiated from a second outer antisense primer selected to specifically hybridize to a sequence in the NS4B-NS5A region of the genome of the prototype HCV and the third reverse transcription reaction initiated from a third outer antisense primer selected to specifically hybridize to a sequence in the NS2 region of the genome of the prototype HCV;
   d) second strand synthesis and amplification of the partial cDNAs of step c) in three separate PCR reactions, the first PCR reaction comprising an aliquot of the first reverse transcription reaction, the first outer antisense primer and a first outer sense primer selected to specifically hybridize to a complementary sequence in the NS4B-NS5A region of the genome of the prototype HCV, the second PCR reaction comprising an aliquot of the second reverse transcription reaction, the second outer antisense primer and a second outer sense primer selected to specifically hybridize to a complementary sequence in the NS2 region of the genome of the prototype HCV, and the third PCR reaction comprising an aliquot of the third reverse transcription reaction, the third outer antisense primer and a third outer sense primer selected to specifically hybridize to a complementary sequence in the 5'UTR region of the genome of the prototype HCV, wherein the second outer antisense primer hybridizes to a sequence in the NS4B-NS5A region of the genome of the prototype HCV that is located 3' to the region that is complementary to the first outer sense primer and wherein the third outer antisense primer hybridizes to a sequence in the NS2 region of the genome of the prototype HCV that is located 3' to the region that is complementary to the second outer sense primer;
   e) further amplification of the partial cDNAs of step d) in three separate nested PCR reactions, the first nested PCR reaction comprising an aliquot of the first PCR reaction and first inner antisense and sense primers, the second nested PCR reaction comprising an aliquot of the second PCR reaction and second inner antisense and sense primers, and the third nested PCR reaction comprising an aliquot of the third PCR reaction and third inner antisense and sense primers, wherein the inner primers do not overlap the outer primers, the second inner antisense primer hybridizes to a sequence in the NS4B-NS5A region of the genome of the prototype HCV that is located 3' to the region that is complementary to the first inner sense primer and the third inner antisense primer hybridizes to a sequence in the NS2 region of the genome of the prototype HCV that is located 3' to the region that is complementary to the second inner sense primer;

f) sequence analysis of the further amplified cDNAs of step e);

g) comparison of the sequences obtained from step f) with that of the prototype HCV and identification of mutations; and h) entry of the mutations identified in a data bank of HCV mutations associated with anti-HCV drug resistance.

3. The assay of claim 2, wherein step h) consists of a search of a data bank of HCV mutations associated with anti-HCV drug resistance for the mutations identified and selection for subsequent treatment of the subject of an anti-HCV drug or drug combination to which the HCV is not expected to be resistant.

4. The assay of claim 3, wherein the sample is taken from a subject infected with HCV prior to commencement of any pharmacological therapy of the subject.

5. An assay for identifying a mutation in the genome of an HCV present in a sample, the assay comprising the sequential steps of:
   a) extraction of viral RNA from the sample containing the HCV;
   b) determination of genotype and subtype of the HCV;
   c) provided that step b) indicated that the HCV is of type 1b, synthesis of partial cDNAs of the genome of the HCV in three separate reverse transcription reactions, the first reverse transcription reaction initiated from primer poly-A (SEQ ID NO: 1), the second reverse transcription reaction initiated from primer HCV1bOR6312 (SEQ ID NO: 2) and the third reverse transcription reaction initiated from primer HCV1bOR3306 (SEQ ID NO: 3);
   d) second strand synthesis and amplification of the partial cDNAs of step c) in three separate PCR reactions, the first PCR reaction comprising an aliquot of the first reverse transcription reaction and primer pair poly-A/HCV1bOF6074 (SEQ ID NOs: 1/4), the second PCR reaction comprising an aliquot of the second reverse transcription reaction and primer pair HCV1bOR6312/HCV1bOF1977 (SEQ ID NOs: 2/5) and the third PCR reaction comprising an aliquot of the third reverse transcription reaction and primer pair HCV1 bOR3306/HCVOF129 (SEQ ID NOs: 3/6);
   e) further amplification of the partial cDNAs of step d) in three separate nested PCR reactions, the first nested PCR reaction comprising an aliquot of the first PCR reaction and primer pair HCV1b1R9339/HCV1b1F6126 (SEQ ID NOs: 7/10), the second nested PCR reaction comprising an aliquot of the second PCR reaction and primer pair HCV1b1R6282/HCV1b1F2523 (SEQ ID NOs: 8/11), and the third nested PCR reaction comprising an aliquot of the third PCR reaction and primer pair HCV1 b1R2770/HCVIF278 (SEQ ID NOs: 9/12);
   f) sequence analysis of the further amplified cDNAs of step e); and
   g) comparison of the sequences obtained from step f) with that of a prototype HCV1b.

6. An assay for identifying and characterizing single and linked mutations in a genome of an HCV resistant to an anti-HCV drug, the assay comprising the sequential steps of:
   a) extraction of viral RNA from a sample taken from a subject harboring an HCV that is resistant to an anti-HCV drug or drug combination with which the subject has been treated;
   b) determination of genotype and subtype of the HCV;
   c) provided that step b) indicated that the HCV is of type 1b, synthesis of partial cDNAs of the genome of the HCV in three separate reverse transcription reactions, the first reverse transcription reaction initiated from primer poly-A (SEQ ID NO: 1), the second reverse transcription reaction initiated from primer HCV1bOR6312 (SEQ ID NO: 2) and the third reverse transcription reaction initiated from primer HCV1bOR3306 (SEQ ID NO: 3);
   d) second strand synthesis and amplification of the partial cDNAs of step c) in three separate PCR reactions, the first PCR reaction comprising an aliquot of the first reverse transcription reaction and primer pair poly-A/HCV1bOF6074 (SEQ ID NOs: 1/4), the second PCR reaction comprising an aliquot of the second reverse transcription reaction and primer pair HCV1bOR6312/HCV1bOF1977 (SEQ ID NOs: 2/5) and the third PCR reaction comprising an aliquot of the third reverse transcription reaction and primer pair HCV1bOR3306/HCVOF129 (SEQ ID NOs: 3/6);
   e) further amplification of the partial cDNAs of step d) in three separate nested PCR reactions, the first nested PCR reaction comprising an aliquot of the first PCR reaction and primer pair HCV1b1R9339/HCV1b1F6126 (SEQ ID NOs: 7/10), the second nested PCR reaction comprising an aliquot of the second PCR reaction and primer pair HCV1b1R6282/HCV1b1F2523 (SEQ ID NOs: 8/11), and the third nested PCR reaction comprising an aliquot of the third PCR reaction and primer pair HCV1b1R2770/HCVIF278 (SEQ ID NOs: 9/12);
   f) sequence analysis of the further amplified cDNAs of step e);
   g) comparison of the sequences obtained from step f) with that of a prototype HCV 1b and identification of mutations; and
   h) entry of the mutations identified in a data bank of HCV mutations associated with anti-HCV drug resistance.

7. The assay of claim 6, wherein step h) consists of a search of a data bank of HCV mutations associated with anti-HCV drug resistance for the mutations identified and selection for subsequent treatment of the subject of an anti-HCV drug or drug combination to which the HCV is not expected to be resistant.

8. The assay of claim 7, wherein the sample is taken from a subject infected with HCV prior to commencement of any pharmacological therapy of the subject.

\* \* \* \* \*